(12) United States Patent
Jeon et al.

(10) Patent No.: US 8,143,262 B2
(45) Date of Patent: Mar. 27, 2012

(54) 7-(3',4'-DIALKOXYPHENYL)[1,2,4]-TRIAZOLO[1,5-A]PYRIMIDINE COMPOUNDS, PROCESS FOR PREPARING THEREOF, AND PHARMACEUTICAL COMPOSITION FOR TREATING OR PREVENTING ASTHMA, CHRONIC OBSTRUCTIVE PULMONARY DISEASE, ARTHRITIS, ATOPIC DERMATITIS, TUMOR AND DEGENERATIVE BRAIN DISEASES COMPRISING THE SAME

(75) Inventors: Dong Ju Jeon, Daejeon (KR); Zaesung No, Chungcheongnam-do (KR); Jong Hwan Song, Chungcheongbuk-do (KR); Gehyeong Lee, Daejeon (KR); Ikyon Kim, Daejeon (KR); Chang Min Park, Gyeongsangbuk-do (KR); Hyae Gyeong Cheon, Daejeon (KR); Young Sik Cho, Daejeon (KR); Jin Sook Song, Daejeon (KR); Myung Ae Bae, Daejeon (KR); Sung-eun Yoo, Chungcheongnam-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 232 days.

(21) Appl. No.: 12/531,818

(22) PCT Filed: Mar. 7, 2008

(86) PCT No.: PCT/KR2008/001278
§ 371 (c)(1),
(2), (4) Date: Sep. 17, 2009

(87) PCT Pub. No.: WO2008/117943
PCT Pub. Date: Oct. 2, 2008

(65) Prior Publication Data
US 2010/0105704 A1    Apr. 29, 2010

(30) Foreign Application Priority Data

Mar. 23, 2007 (KR) ........................ 10-2007-0028620

(51) Int. Cl.
*A01N 43/90* (2006.01)
*A61K 31/519* (2006.01)
*C07D 487/00* (2006.01)
(52) U.S. Cl. ..................................... 514/262.1; 544/263
(58) Field of Classification Search ........................ None
See application file for complete search history.

(56) References Cited

OTHER PUBLICATIONS

Petrich, et al., The Application of Unsymmetrical Vinylogous Iminium Salts and Related Synthons to the Preparation of Monosubstituted Triasolo [1,5-a] pyrimidines, Tetrahedron, Elsevier Science Publishers, (Jan. 1, 1994), vol. 50, No. 42, pp. 12113-12124.*

Petrich et al., The Application of Unsymmetrical Vinylogous Iminium Salts and Related Synthons to the Preparation of Monosubstituted Triasolo [1,5-a] pyrimidines, Tetrahedron, Elsevier Science Publishers, (Jan. 1, 1994), vol. 50, No. 42, pp. 12113-12124.

* cited by examiner

*Primary Examiner* — Jeffrey Murray
(74) *Attorney, Agent, or Firm* — The Webb Law Firm

(57) ABSTRACT

The present invention relates to novel {7-(3',4'-dialkoxyphenyl)-[1,2,4]-triazolo[1,5-a]pyrimidine compounds or pharmaceutically acceptable salts thereof, a process for preparing the same, and pharmaceutical compositions for treating or preventing inflammatory diseases including asthma and chronic obstructive pulmonary disease, arthritis, atopic dermatitis, cancers including leukemia, and degenerative brain diseases including Alzheimer's disease, depression and memory impairment, which comprises the same as an active ingredient.

7 Claims, 2 Drawing Sheets

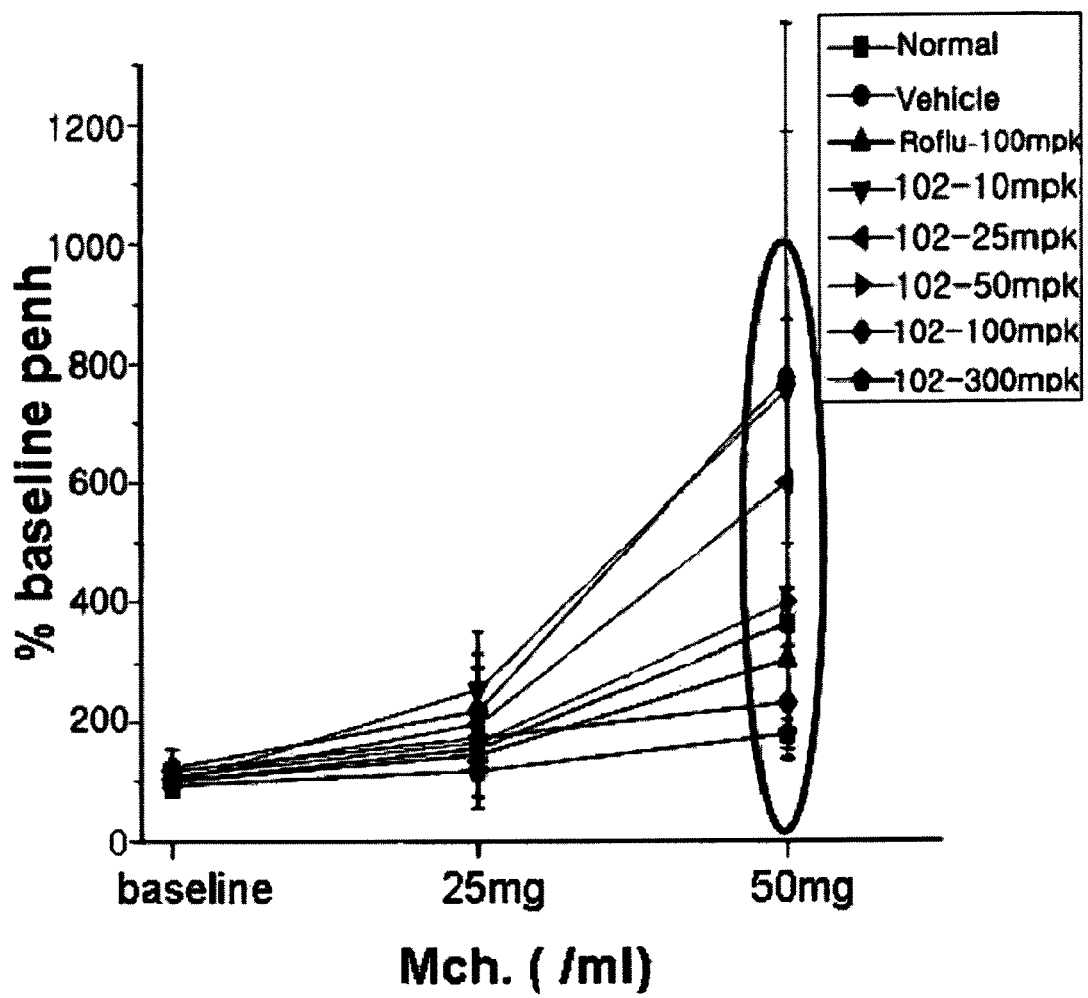
[Fig. 1]

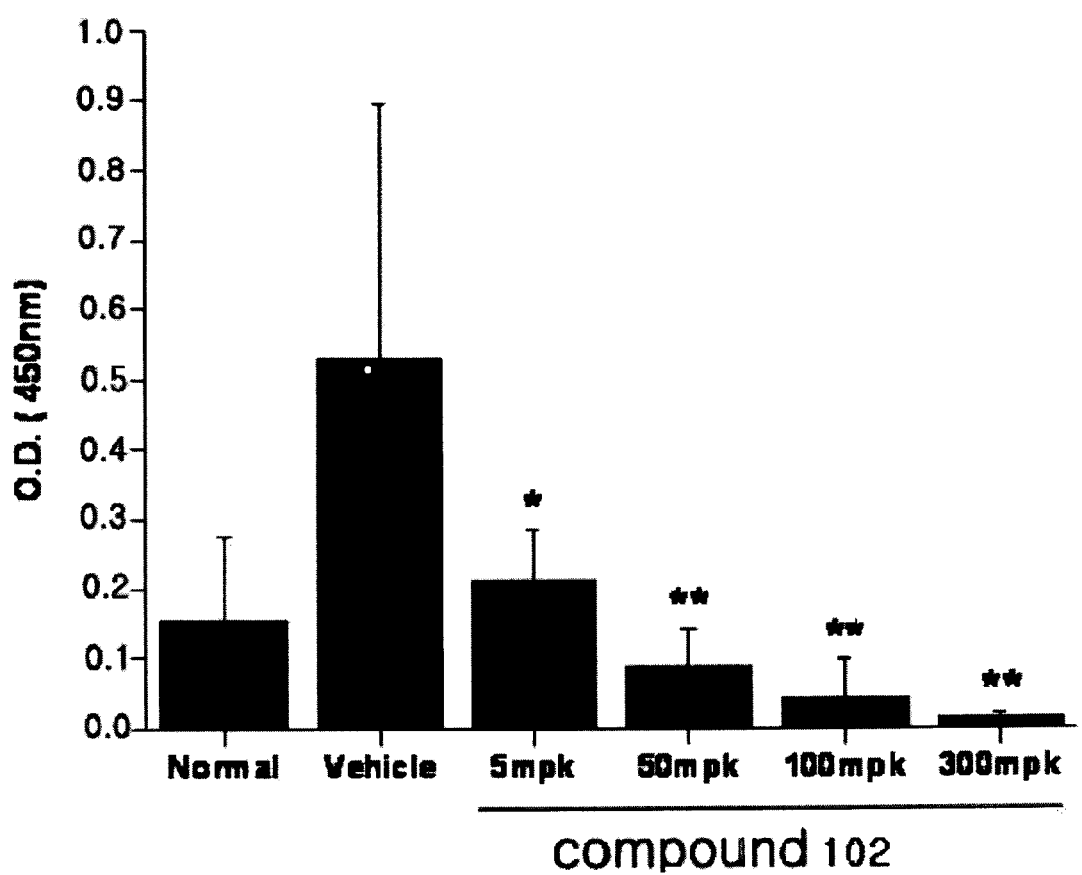
[Fig. 2]

7-(3',4'-DIALKOXYPHENYL)[1,2,4]-TRIAZOLO[1,5-A]PYRIMIDINE COMPOUNDS, PROCESS FOR PREPARING THEREOF, AND PHARMACEUTICAL COMPOSITION FOR TREATING OR PREVENTING ASTHMA, CHRONIC OBSTRUCTIVE PULMONARY DISEASE, ARTHRITIS, ATOPIC DERMATITIS, TUMOR AND DEGENERATIVE BRAIN DISEASES COMPRISING THE SAME

TECHNICAL FIELD

The present invention relates to novel 7-(3',4'-dialkoxyphenyl)-[1,2,4]-triazolo[1,5-a]pyrimidine compounds or pharmaceutically acceptable salts thereof, a process for preparing the same, and pharmaceutical compositions for treating or preventing inflammatory diseases including asthma and chronic obstructive pulmonary disease, arthritis, atopic dermatitis, cancers including leukemia, and degenerative brain diseases including Alzheimer's disease, depression and memory impairment, which comprises the same as an active ingredient.

BACKGROUND ART

Various compounds have been investigated as PDE-4 inhibitors, on which the present invention is based, in order to develop therapeutic agent for asthma and chronic obstructive pulmonary diseases [Peter Norman, *Expert Opin. Ther. Patents.* 2002, 12(1), pp 93-111]. Among them, the most representative compounds are Rolipram [EP 0660711, Jul. 5, 1995], Cilomilast [U.S. Pat. No. 6,013,827, Jan. 11, 2000] and Roflumilast [U.S. Pat. No. 5,712,298, Jan. 27, 1998].

Development of Rolipram, which had been firstly advanced into clinical studies, was ceased owing to its insignificant clinical effect and side effects such as vomiting.

Development of Cilomilast as a therapeutic agent for asthma was also ceased owing to its insufficient therapeutic effect on asthma, resulted of clinical studies. Clinical studies on chronic obstructive pulmonary disease (COPD) of the same compound are in progress [Peter Norman, *Expert Opin. Ther. Patents* 2002, 12(1), 93-111; Compton C, Edelson J D., Cedar E., *Am. J. Respir. Crit. Care Med.* 2001, 163, A909].

Roflumilast developed by Altana (Germany) has been known as the most effective compound [Zheng Huang, Yves Ducharme, Dwight Macdonald and Annette Robichaud, *Current Opinion in Chemical Biology* 2001, 5, 432-438], which showed excellent effect of inhibiting PDE-4 ($IC_{50}$=0.8 nM), and noticeable effect on asthma and COPD in animal test [Armin Hatzelman and Christian Schudt, *The Journal of Pharmacology and Experimental Therapeutics* 2000, 297(1), 267-279; Daniela S. Bundschuh, Manfrid Eltze, Johannes Barsig, Lutz Wollin, Armin Hatzelmann, and Rolf Beume, *The Journal of Pharmacology and Experimental Therapeutics* 2001, 297(1), 280-290]. However, the approval as a therapeutic agent for asthma in Europe was withdrawn in 2005.

It has been also known that PDE-4 inhibitors also show effect of treating arthritis (USP 2003/0092706 A1), therapeutic effect on atopic dermatitis, leukemia, various cancers (Miles D. Houslay, Peter Schafer and Kam Y. J. Zhang, *Drug Discovery Today,* 2005, 10(22), 1503-1519) and effect of treating depression (U.S. Pat. No. 4,178,449, Dec. 11, 1979), and therapeutic effect on degenerative brain diseases such as Alzheimer's disease (Sophie L. Rovner, C&EN, 38, Feb. 21, 2005), as well as therapeutic effect on inflammatory pulmonary diseases such as asthma and chromic obstructive pulmonary disease.

Synthesis of 7-aryl-[1,2,4]-triazolo[1,5-a]pyrimidine derivatives, having similar structure to that of compound of Chemical Formula (1) according to the present invention has been reported (U.S. Pat. No. 5,127,936 (1992); U.S. Pat. No. 4,209,621 (1980)). But the compounds are not connected to preventing or treating asthma and chronic obstructive pulmonary disease, arthritis, atopic dermatitis, various cancers including leukemia and degenerative brain diseases.

Further, WO 06/071752 discloses triazolopyrimidine compounds represented by Chemical Formula (A), wherein methylamino or ethylamino group has been incorporated to 6-position of triazolopyrimidine. But the compounds simply include the compounds wherein dichlorophenyl is incorporated to Y, or the like. The disclosure relates to studies on therapeutic agent for diabetes, not to preventing or treating asthma and chronic obstructive pulmonary disease, arthritis, atopic dermatitis, various cancers including leukemia and degenerative brain diseases.

[Chemical Formula A]

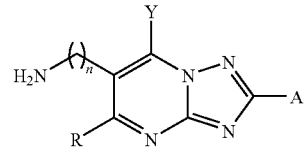

In addition, WO 02/02563 discloses triazolopyrimidine compounds (such as compounds represented by Chemical Formula B) having the similar structure to that of the compounds according to the present invention. However, the disclosure relates to only the studies on the compounds wherein mostly is a heterocyclic group (including very few cases wherein $R_1$ is phenyl), without substantial studies on the compounds wherein $R_1$ is a 3,4-dialkoxyphenyl. The studies simply relate to the compounds wherein at least one of $R_2$ and $R_3$ is (are) substituted by a substituent other than hydrogen, without studies on the compounds wherein both $R_2$ and $R_3$ are hydrogen. Moreover, with respect to the effect, the patent application describes only anticancer effect, but with no description about any effect of preventing or treating asthma and chronic obstructive pulmonary disease, arthritis, atopic dermatitis and degenerative brain diseases. Particularly, there is no substantial studies on 7-(3',4'-dialkoxyphenyl)-[1,2,4]triazolo[1,5-a]pyrimidine compounds of the present invention.

[Chemical Formula B]

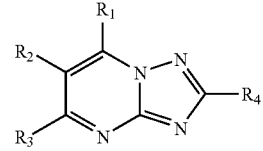

DISCLOSURE OF INVENTION

Technical Problem

In order to develop therapeutic agent with excellent effects in vitro and in vivo, for inflammatory diseases including asthma and chronic obstructive pulmonary diseases, arthritis, atopic dermatitis, cancers and degenerative brain diseases, based on inhibition of PDE-4, while overcoming the relevant side effects such as vomiting and headache (as the disadvantages of PDE-4 inhibitors), the present inventors prepared novel 7-(3',4'-dialkoxyphenyl)-[1,2,4]triazolo[1,5-a]pyrimidine compounds. The compounds according to the present invention exhibited excellent effect of inhibiting PDE-4 enzyme and high enzyme specificity as the results of biochemical and pharmacological experiments, as well as excellent effect of treating asthma in vivo and treating rheumatic arthritis, from the disease model animal test by means of oral administration. It was also confirmed that there was no side effects such as vomiting, diarrhea and salivation from the test using ferret animal models.

Thus, the object of the present invention is to provide novel 7-(3',4'-dialkoxyphenyl)-[1,2,4]triazolo[1,5-a]pyrimidine compounds and pharmaceutically acceptable salts thereof. Additional objects of the present invention is to provide a process for preparing novel 7-(3',4'-dialkoxyphenyl)-[1,2,4]triazolo[1,5-a]pyrimidine compound according to the present invention, and to provide a pharmaceutical composition for treating and preventing inflammatory diseases including asthma and chronic obstructive pulmonary disease, arthritis, atopic dermatitis, cancers including leukemia, and degenerative brain diseases including Alzheimer's disease, depression and memory impairment, which comprises the same as an active ingredient.

Technical Solution

The present invention relates to novel 7-(3',4'-dialkoxyphenyl)-[1,2,4]-triazolo[1,5-a]pyrimidine compounds represented by Chemical Formula (1) or pharmaceutically acceptable salts thereof, a process for preparing the same, and pharmaceutical compositions for treating or preventing inflammatory diseases including asthma and chronic obstructive pulmonary disease, arthritis, atopic dermatitis, cancers including leukemia, and degenerative brain diseases including Alzheimer's disease, depression and memory impairment, which comprises the same as an active ingredient.

[Chemical Formula 1]

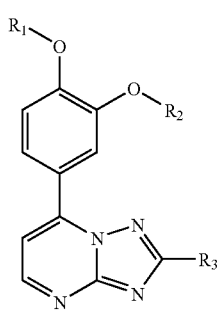

In Chemical Formula (1), $R_1$ and $R_2$, being same or different, independently represent hydrogen atom, a linear or branched, saturated or unsaturated $(C_1-C_7)$alkyl, a linear or branched, saturated or unsaturated $(C_1-C_7)$alkyl containing oxygen, nitrogen or sulfur, $(C_3-C_7)$cycloalkyl, $(C_3-C_7)$cycloalkyl containing oxygen, nitrogen or sulfur, $(C_3-C_7)$cycloalkyl$(C_1-C_7)$alkyl, 3- to 7-membered saturated or unsaturated heterocycloalkyl containing oxygen, nitrogen or sulfur in the heterocyclic ring, 3- to 7-membered saturated or unsaturated heterocycloalkyl$(C_1-C_7)$alkyl containing oxygen, nitrogen or sulfur in the heterocyclic ring, phenyl or benzyl, or $R_1$ and $R_2$ may be linked via $(C_1-C_3)$ alkylene or $(C_1-C_3)$ alkylene containing halogen;

$R_3$ represents hydrogen atom, formyl, halogen, a linear or branched saturated or unsaturated $(C_1-C_7)$alkyl, $(C_1-C_7)$alkoxy, $(C_3-C_7)$cycloalkyl, $(C_1-C_7)$alkoxy$(C_1-C_7)$alkyl, $(C_1-C_7)$alkylketone, hydroxy$(C_1-C_7)$alkyl, $(C_3-C_7)$cycloalkyl $(C_1-C_7)$alkyl, $(C_3-C_7)$cycloalkyl$(C_1-C_7)$alkoxy, $(C_1-C_7)$alkylcarboxylic acid, carboxyl$(C_1-C_{10})$alkylester, carboxyl$(C_1-C_{10})$alkylamide, amino, mono or di$(C_1-C_7)$alkylamino, mono or di$(C_1-C_7)$alkylaminocarbonyl, $(C_3-C_7)$cycloalkylamino, morpholine, morpholine oxide, thiomorpholine, piperidine, piperazine, piperazine oxide, piperidine, piperidine oxide, pyrrolidine, cyano, nitro, carboxylic acid, guanidine, urea, phenoxy, benzyloxy or an aryl group represented by following Chemical Formulas:

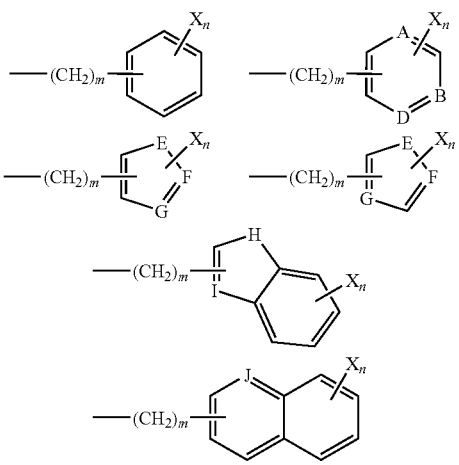

wherein, A is N or NO; B is CH or N; D is CH or N; E is S, O or NH; F is CH or N; G is CH or N; H is S, O or NH; I is CH or N; J is CH, N or NO; and m and n independently represent an integer from 0 to 4;

X, being same or different, independently represents a linear or branched, saturated or unsaturated $(C_1-C_7)$alkyl, $(C_1-C_7)$alkoxy, $(C_1-C_7)$alkylthio, thiol, $(C_6-C_{10})$arylthio, $(C_1-C_7)$alkylsulfinyl, $(C_6-C_{10})$arylsulfinyl, $(C_1-C_7)$alkylsulfonyl, $(C_1-C_{10})$arylsulfonyl, $(C_1-C_7)$alkoxy$(C_1-C_7)$alkyl, $(C_1-C_7)$alkoxycarbonyl, $(C_1-C_7)$alkoxycarbonyl$(C_1-C_7)$alkoxy, $(C_1-C_7)$alkoxycarbonyl$(C_1-C_7)$alkylamino, $(C_1-C_7)$alkoxycarbonyl$(C_1-C_7)$alkylaminocarbonyl, $(C_1-C_7)$alkylcarbonyloxy$(C_1-C_7)$alkoxycarbonyl, hydroxy, halogen, cyano, nitro, amino, mono or di$(C_1-C_7)$alkylamino, mono or di$(C_6-C_{10})$arylamino, mono or di$(C_1-C_7)$alkylaminocarbonyl, mono or dibenzylamino, mono or di$(C_1-C_7)$alkylamino$(C_1-C_7)$alkoxy, $(C_3-C_7)$cycloalkylamino, $(C_1-C_7)$alkylcarbonylamino, $(C_1-C_7)$alkylsulfinylamino, $(C_1-C_7)$alkylsulfonylamino, $(C_6-C_{10})$arylsulfinylamino, $(C_6-C_{10})$arylsulfonylamino, benzylsulfinylamino, benzylsulfonylamino, aminosulfonylamino, $(C_1-C_7)$alkylaminosulfonylamino, $(C_6-C_{10})$arylaminosulfonylamino, aminocarbonyl, 3- to 7-membered saturated or unsaturated heterocycloalkyl containing at least one oxygen, nitrogen or sulfur atom(s) in the heterocyclic ring, morpholine, morpholine oxide, piperazine, piperazine oxide, $(C_1-C_7)$alkylpiperazine, $(C_1-C_7)$alkylpiperazinoxide, guanidine, urea, hydrazine, $(C_1-C_7)$alkylhydrazine, di$(C_1-C_7)$alkylhydrazine, $(C_6-C_{10})$arylhydrazine, benzylhydrazine, dibenzylhydrazine, hydroxylamine, $(C_1-C_7)$alkylhydroxylamine, $(C_6-C_{10})$arylhydroxylamine, oxime, $(C_1-C_7)$alkyloxime, $(C_6-C_{10})$aryloxime, $(C_1-C_7)$alkylguanidine, $(C_1-C_7)$alkylurea, phenyl, phenoxy, benzyl, benzyloxy, thiobenzyl, carboxylic acid, carboxyl$(C_1$ $C_7$)alkylamino, carboxyl($C_1$ $C_{10}$)alkylaminocarbonyl, ($C_1$ $C_7$)alkylcarbonyl, ($C_1$ $C_7$)alkylketone or benzoyl;

provided that ($C_1$ $C_7$)alkyl, ($C_1$ $C_7$)alkoxy, ($C_3$ $C_7$)cycloalkyl, ($C_3$ $C_7$)cycloalkyl($C_1$ $C_7$)alkyl, heterocycloalkyl, phenyl or benzyl in $R_1$, $R_2$, $R_3$ and X may be substituted with ($C_1$ $C_7$)alkoxy, halogen, nitro, cyano, hydroxy, amino, mono or di($C_1$ $C_7$)alkylamino, ($C_1$ $C_{10}$)alkoxycarbonyl, carboxyl ($C_1$ $C_{10}$)alkylamide, guanidine, ($C_1$ $C_7$)alkylguanidine, urea, ($C_1$ $C_7$)alkylurea, ($C_1$ $C_7$)alkylcarbonylamino or carboxylic acid.

The compounds, 7-(3',4'-dialkoxyphenyl)-[1,2,4]triazolo[1,5-a]pyrimidine represented by Chemical Formula (1) according to the present invention are novel compounds, which have excellent activity and specificity on PDE-4 enzymes. Exhibiting excellent effects in vivo from animal tests, they are useful for treating or preventing inflammatory diseases including asthma and chronic obstructive pulmonary disease, arthritis, atopic dermatitis, cancers including leukemia, and degenerative brain diseases including Alzheimer's disease, depression and memory impairment.

Specific examples of 7-(3',4'-dialkoxyphenyl)-[1,2,4]triazolo[1,5-a]pyrimidine compounds represented by Chemical Formula (1) according to the present invention are characterized in that $R_1$ and $R_2$, being same or different, independently represent hydrogen atom, a linear or branched, saturated or unsaturated ($C_1$-$C_7$)alkyl, a linear or branched, unsaturated ($C_1$-$C_7$)alkyl containing halogen atom(s), ($C_3$ $C_7$)cycloalkyl or ($C_1$ $C_7$)cycloalkyl($C_1$ $C_7$)alkyl.

Preferable compounds represented by Chemical Formula (1) according to the present invention include those compounds wherein $R_1$ is a linear or branched, saturated or unsaturated ($C_1$-$C_7$)alkyl, or a linear or branched, unsaturated ($C_1$-$C_7$)alkyl containing halogen atom(s); $R_2$ is linear or branched, saturated or unsaturated ($C_1$-$C_7$)alkyl, cyclopropyl, cyclopentyl or cyclopropylmethyl; X is a linear or branched, saturated or unsaturated ($C_1$ $C_7$)alkyl, linear or branched, unsaturated ($C_1$ $C_7$)alkyl containing halogen atom(s), ($C_1$ $C_7$)alkoxy, ($C_1$ $C_7$)alkylthio, ($C_1$ $C_7$)alkoxycarbonyl, hydroxy, halogen, cyano, nitro, amino, mono or di($C_1$ $C_7$)alkylamino, mono or di($C_1$ $C_7$)alkylaminocarbonyl, ($C_1$ $C_7$)alkylcarbonylamino, aminocarbonyl, phenyl, phenoxy, benzyl, benzyloxy, thiobenzyl or carboxylic acid; and n is an integer from 0 to 3.

Particularly preferable compounds of the present invention include those represented by Chemical Formula (2):

[Chemical Formula 2]

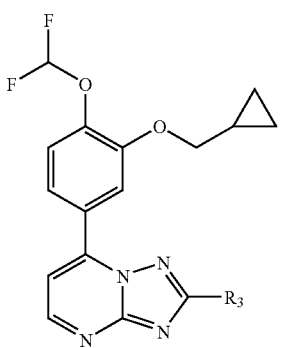

wherein, $R_3$ is an aryl group represented by one of the following Chemical Formulas:

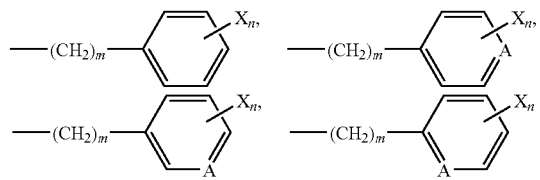

wherein, A is N or NO;

m and n independently represent an integer from 0 to 3; and X, being same or different, independently represents a linear or branched, saturated or unsaturated ($C_1$ $C_7$)alkyl, a linear or branched, unsaturated ($C_1$ $C_7$)alkyl containing halogen atom(s), ($C_1$ $C_7$)alkoxy, ($C_1$ $C_7$)alkylthio, ($C_1$ $C_7$)alkoxycarbonyl, halogen, cyano, nitro, amino, aminocarbonyl or carboxylic acid.

The most preferable compounds according to the present invention include, among the compounds represented by Chemical Formula (2), those represented by Chemical Formula (3) wherein X is ($C_1$ $C_7$)alkoxy, halogen, cyano, nitro, amino or carboxylic acid, and A represents N or NO.

[Chemical Formula 3]

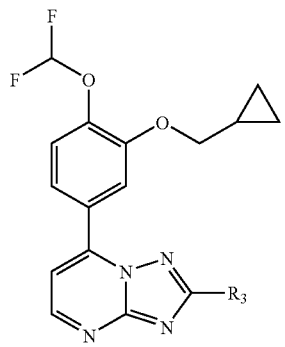

In the Chemical Formula, $R_3$ is an aryl group represented by one of the following

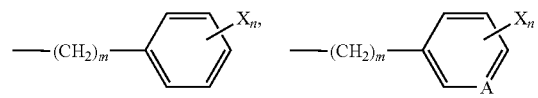

wherein, A is N or NO;

m and n independently represent an integer of 0 or 1; and X, being same or different, independently represents ($C_1$ $C_7$)alkoxy, halogen, cyano, nitro, amino or carboxylic acid.

Representative compounds of Chemical Formula (3) include:

7-[3-(cyclopropylmethoxy)-(difluoromethoxy)phenyl]-2-(pyridin-3-yl)-[1,2,4]triazolo[1,5-a]pyrimidine 3-[7-{3-(cyclopropylmethoxy)-4-(difluoromethoxy)phenyl}-[1,2,4]triazolo[1,5-a]pyrimidin-2-yl]-pyridinium chloride 7-[3-(cyclopropylmethoxy)-(difluoromethoxy)phenyl]-2-(3-methoxyphenyl)-[1,2,4]triazolo[1,5-a]pyrimidine 3-[7-{3-(cyclopropylmethoxy)-4-(difluoromethoxy)phenyl}-[1,2,4]triazolo[1,5-a]pyrimidine-2-yl]-pyridine-N-oxide 7-[3-(cyclopropylmethoxy)-4-(difluoromethoxy)phenyl]-2-(3-iodophenyl)-[1,2,4]triazolo[1,5-a]pyrimidine 2-(3-cyanophenyl)-7-[3-(cyclopropylmethoxy)-4-(difluoromethoxy)phenyl]-[1,2,4]triazolo[1,5-a]pyrimidine
3-[7-{3-(cyclopropylmethoxy)-4-(difluoromethoxy)phenyl}-[1,2,4]triazolo[1,5-a]pyrimidin-2-yl]benzoic acid
2-(3-aminophenyl)-7-[3-(cyclopropylmethoxy)-4-(difluoromethoxy)phenyl]-[1,2,4]triazolo[1,5-a]pyrimidine.

As the processes for preparing compounds represented by Chemical Formula (1) according to the present invention, exemplified are Reaction Scheme (1) and Reaction Scheme (2), but the processes for preparing compounds of Chemical Formula (1) are not restricted thereto. But modifications of the processes are obvious to a person having ordinary skill in the art, and the definitions of the substituents in the Reaction Schemes are identical to those defined in Chemical Formula (1).

As illustrated by Reaction Scheme (1), the process for preparing 7-(3',4'-dialkoxyphenyl)-[1,2,4]triazolo[1,5-a]pyrimidine compound represented by Chemical Formula (1) comprises reacting 3-amino-triazole compound (4) with 3-(dimethylamino)-1-(3,4-dialkoxyphenyl)propenone compound (5) in the presence of acetic acid to obtain 7-(3',4'-dialkoxyphenyl)-[1,2,4]triazolo[1,5-a]pyrimidine compound of Chemical Formula (1).

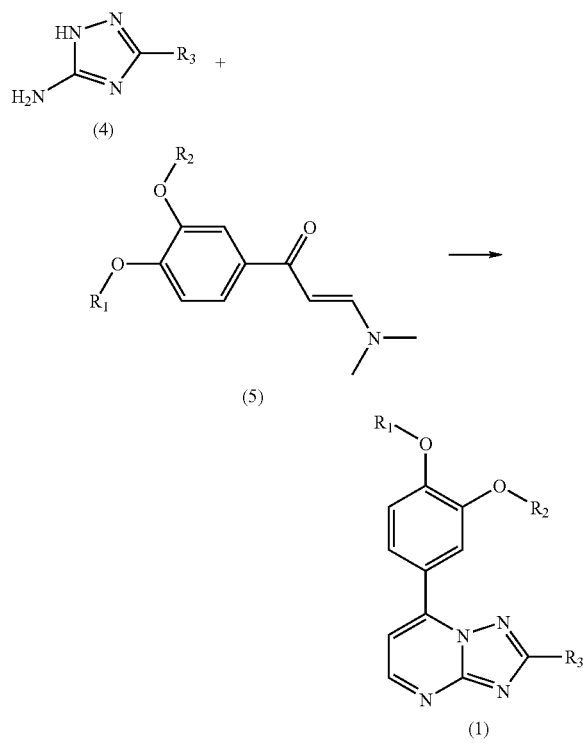

In the Chemical Formulas, $R_1$, $R_2$ and $R_3$ are defined as in Chemical Formula (1).

In the process for preparing 7-(3',4'-dialkoxyphenyl)-[1,2,4]triazolo[1,5-a]pyrimidine compound represented by Chemical Formula (1) from 3-amino-triazole compound (4) and 3-(dimethylamino)-1-(3,4-dialkoxyphenyl)propenone compound (5), a base such as piperidine and alcohol may be used (K. M. Al-Zaydi, M. A. A. Al-Shiekh, E. A. A. Hafez, *J. Chem. Res. Synop*, 2000, 1, 13-15. E. I. Al-Afaleq, *Synth Commun*, 2000, 30 (11), 1985 1999), but acetic acid is more preferably used as solvent.

An alternative process for preparing 7-(3',4'-dialkoxyphenyl)-[1,2,4]triazolo[1,5-a]pyrimidine compound of Chemical Formula (1) comprises reacting 3-amino-triazole compound (4) with 3-(3,4-dialkoxyphenyl)-3-oxopropionaldehyde compound (6) in the presence of acetic acid to obtain 7-(3',4'-dialkoxyphenyl)-[1,2,4]triazolo[1,5-a]pyrimidine compound of Chemical Formula (1), as shown in Reaction Scheme (2).

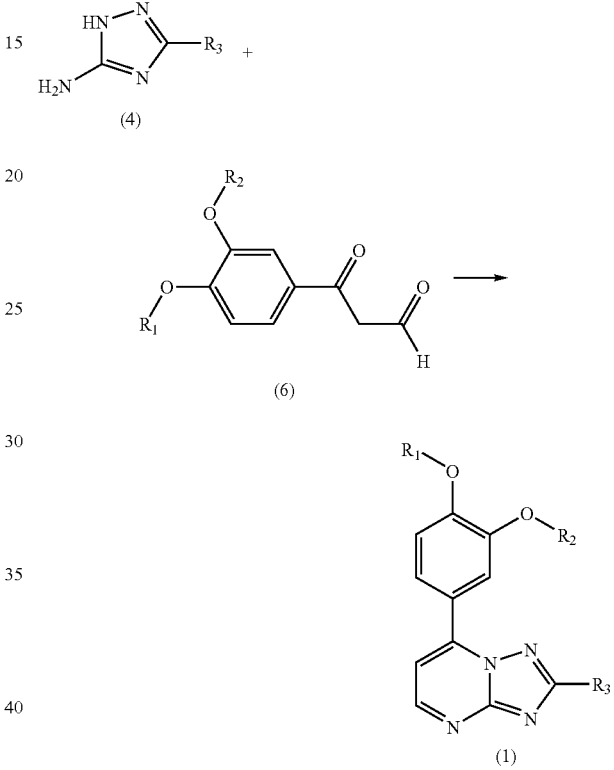

In the Chemical Formulas, $R_1$, $R_2$ and $R_3$ are defined as in Chemical Formula (1).

The starting material for preparing compound of Chemical Formula (1), 3-amino-triazole compound (4) can be prepared by reacting a substituted ester compound (7) with aminoguanidine, or reacting a substituted hydrazide (8) with S-methyl thiourea; and 3-(dimethylamino)-1-(3,4-dialkoxyphenyl)propenone compound (5) can be prepared by reacting catechol ketone compound (9) with acetal of dimethylformamide (DMF-acetal), as illustrated by Reaction Scheme (3).

[Reaction Scheme 3]

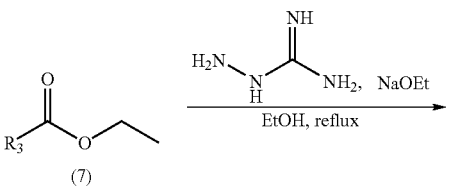

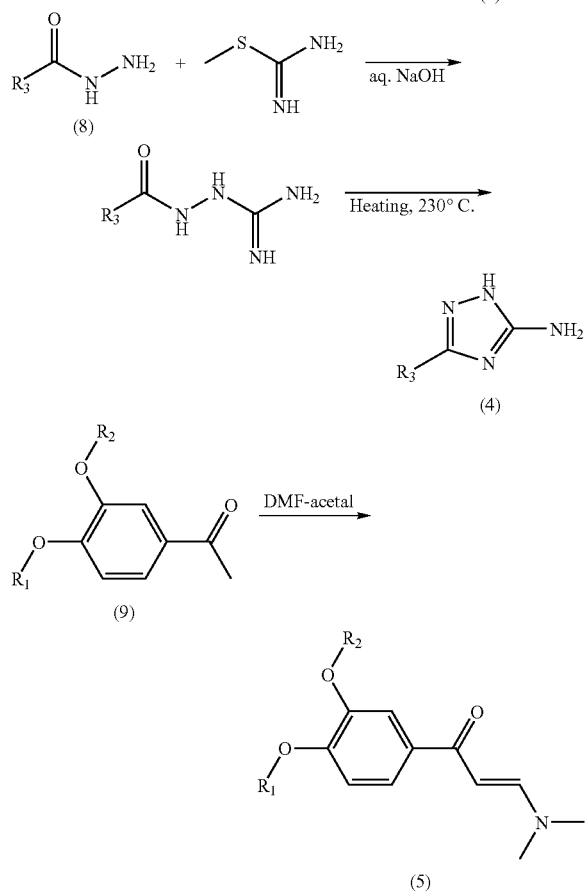

In the Chemical Formulas, $R_1$, $R_2$ and $R_3$ are defined as in Chemical Formula (1).

In the process for preparing 3-amino-triazole compound (4) from substituted ester compound (7) and aminoguanidine, alcohol or the like may be essentially used as solvent. The process for preparing 3-(dimethylamino)-1-(3,4-dialkoxyphenyl)propenone compound (5) from catechol ketone compound (9) and DMF-acetal can be carried out according to a similar process disclosed by prior art (F. Al-Omran, N. Al-Awadhi, M. M. Abdel Khalik, K. Kaul, A. A. El-Khair, and M. H. Elnadgi, *J. Chem. Res, Synop*, 1997, 3, 84-85), wherein DMF-acetal is employed as a reactant and solvent at the same time. The reaction process is not restricted thereto, but the compound may be synthesized via other procedures.

Since 7-(3',4'-dialkoxyphenyl)-[1,2,4]triazolo[1,5-a]pyrimidine compound represented by Chemical Formula (1) prepared according to the present invention has excellent activity and specificity of inhibiting PDE-4 enzyme and low affinity to HARBS from the results of biochemical and pharmacological experiments, it is anticipated that the compound has insignificant side effects such as vomiting. It is confirmed that the compound has excellent effect of treating asthma and rheumatic arthritis from disease model animal tests, and the compound has no side effect such as vomiting or diarrhea from the test for side effect using ferret animal model.

The compounds represented by Chemical Formula (1) according to the present invention are suitable for pharmaceutical compositions for treating or preventing inflammatory diseases including asthma and chronic obstructive pulmonary disease, arthritis, atopic dermatitis, cancers including leukemia, and degenerative brain diseases including Alzheimer's disease, depression and memory impairment.

Pharmaceutically acceptable salts of compound of Chemical Formula (1) include salts formed from both organic or inorganic acid and base. Pharmaceutically acceptable acid addition salts include those derived from hydrochloric acid, bromic acid, sulfuric acid, citric acid, tartaric acid, phosphoric acid, lactic acid, pyruvic acid, acetic acid, trifluoroacetic acid, triphenylacetic acid, phenylacetic acid, substituted phenylacetic acid such as methoxyphenyl acetic acid, sulfamic acid, sulfanylic acid, succinic acid, oxalic acid, fumaric acid, maleic acid, malic acid, glutamic acid, aspartic acid, oxaloacetic acid, methanesulfonic acid, ethanesulfonic acid, arylsulfonic acid (such as p-toluenesulfonic acid, benzenesulfonic acid, naphthalenesulfonic acid or naphthalenedisulfonic acid), salicylic acid, glutaric acid, gluconic acid, tricavalylic acid, mandelic acid, cinnamic acid, substituted cinnamic acid (such as methyl, methoxy, halogen or phenyl substituted cinnamic acid, including 4-methyl and 4-methoxycinnamic acid and α-phenyl cinnamic acid), ascorbic acid, oleic acid, naphthoic acid, hydroxynaphthoic acid (such as 1- or 3-hydroxy-2-naphthoic acid), naphthalenacrylic acid (such as naphthalen-2-acrylic acid), benzoic acid, 4-methoxybenzoic acid, 2- or 4-hydroxybenzoic acid, 4-chlorobenzoic acid, 4-phenylbenzoic acid, benzeneacrylic acid (such as 1,4-benzenediacrylic acid) and isethionic acid.

Pharmaceutically acceptable base salts include ammonium salt, alkali metal salt such as sodium or potassium salt, alkaline earth metal salt such as calcium and magnesium salt, and salts with organic base such as dicyclohexylamine and N-methyl-D-glucamine.

The compounds according to the present invention have potency of achieving the effect of long-term sustaining and immediate initiation of the activity. Certain compounds represent enhanced therapeutic indications in animal model as compared to current long-term sustaining PDE-4 inhibitors. The compounds according to the invention may be suitable for administration of once to three times per day.

The amount of compound of Chemical Formula (1) or pharmaceutically acceptable salts thereof for achieving therapeutic effect may, of course, depend on specific compound, method of administration, subject to be treated, and disease or disorder to be treated, and the compound may be administered orally, intravenously or inhalantly.

Though compound of Chemical Formula (1) according to the present invention or pharmaceutically acceptable salt thereof may be administered alone, it is preferably administered in a pharmaceutical formulation. Thus, the present invention preferably provides pharmaceutical formulations comprising compound of Chemical Formula (1) or pharmaceutically acceptable salt thereof, and pharmaceutically acceptable carrier or vehicle, and optionally one or more therapeutic ingredient(s).

BRIEF DESCRIPTION OF THE DRAWINGS

FIG. 1 is a graph showing the results of inhibiting airway contraction in vivo (Penh) of Compound (102).

FIG. 2 is a graph comparing the ability of Compound (102) for inhibiting eosinophil peroxidase activity (EPO activity).

MODE FOR THE INVENTION

Now the present invention is illustrated in more detail by referring to specific examples. However, the present invention is not restricted by those examples, and it is apparent to a person having ordinary skill in the art that various alterations and modifications can be made within the spirit and scope of the invention.

PREPARATION EXAMPLE 1

Preparation of 1-[3-(cyclopropylmethoxy)-4-(difluoromethoxy)phenyl]-3-(dimethylamino)prop-2-en-1-one

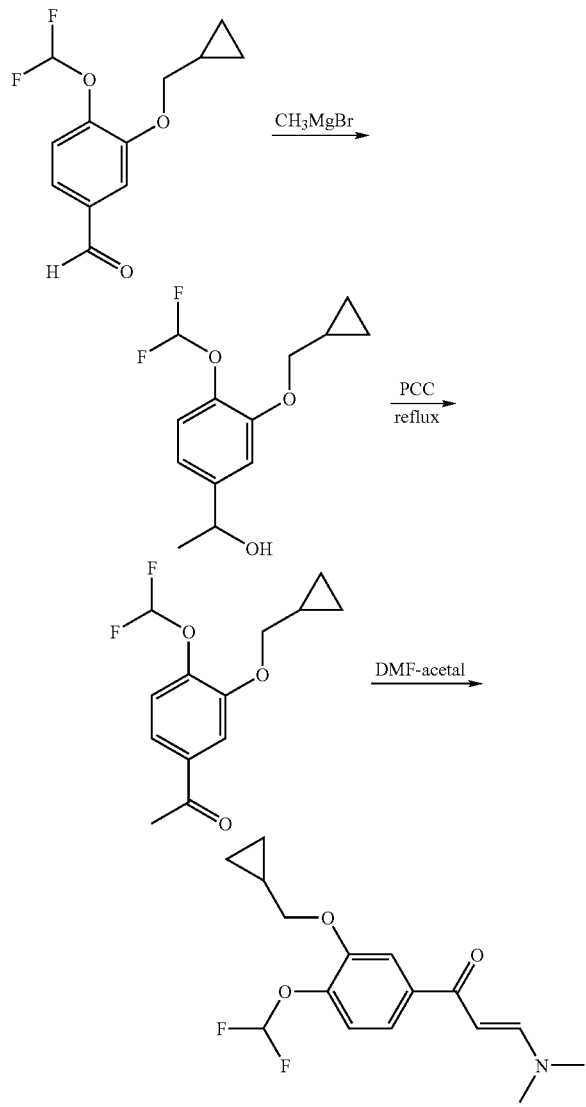

Preparation of 1-[3-(cyclopropylmethoxy)-4-(difluoromethoxy)phenyl]ethanol

In THF, dissolved was 3-(cyclopropylmethoxy)-4-(difluoromethoxy)benzaldehyde (24 g, 99 mmol), and 3M CH$_3$MgBr (49 ml, 148 mmol) was added thereto at −78° C. The reaction mixture was neutralized with NH$_4$Cl, and extracted with EA. The extract was washed twice with brine, dried over MgSO$_4$, filtered and evaporated under reduced pressure to remove solvent. The mixture was purified via column chromatography (n-hexane/EA=1/1) to obtain 1-[3-(cyclopropylmethoxy)-4-(difluoromethoxy)phenyl]ethanol (24 g, 94%).

$^1$H NMR (500 MHz, CDCl$_3$) δ 7.08 (1H, d, J=8.2 Hz, Ar), 6.96 (1H, s, Ar), 6.83 (1H, m, Ar), 6.59 (1H, t, J=74.8 Hz, —CHF$_2$), 4.77 (1H, d, J=5.1 Hz, —CH—), 3.85 (2H, d, J=6.9 Hz, —OCH$_2$—), 1.41 (3H, d, J=6.4 Hz, —CH$_3$), 1.27 (1H, m, —CH—), 0.62 (2H, m, —CH$_2$—), 0.33 (2H, m, —CH$_2$—).

Preparation of 1-[3-(cyclopropylmethoxy)-4-(fluoromethoxy)phenyl]ethanone

In dry MC, dissolved was 1-[3-(cyclopropylmethoxy)-4-(difluoromethoxy)phenyl]ethanol (24 g, 93 mmol), and PCC (pyridinium chlorochromate) (30 g, 139 mmol) was added thereto. The resultant mixture was heated under reflux. The reaction mixture was filtered through Celite, and the filtrate was extracted with EA, washed twice with brine, dried over MgSO$_4$ and filtered. After removing the solvent by evaporation under reduced pressure, the mixture was purified via column chromatography (n-hexane/MC=7/1) to obtain 1-[3-(cyclopropylmethoxy)-4-(difluoromethoxy)phenyl]ethanone (19 g, 91%).

$^1$H NMR (500 MHz, CDCl$_3$) δ 7.56 (1H, s, Ar), 7.52 (1H, m, Ar), 7.21 (1H, d, J=8.2 Hz, Ar), 6.73 (1H, t, J=74.7 Hz, —CHF$_2$), 3.93 (2H, d, J=7.2 Hz, —OCH$_2$—), 2.58 (3H, s, —CH$_3$), 1.30 (1H, m, —CH—), 0.66 (2H, m, —CH$_2$—), 0.37 (2H, m, —CH$_2$).

Preparation of 1-[3-(cyclopropylmethoxy)-4-(difluoromethoxy)phenyl]-3-(dimethylamino)prop-2-en-1-one In toluene, dissolved were 1-[3-(cyclopropylmethoxy)-4-(difluoromethoxy)phenyl]ethanone (10 g, 39 mmol) and DMFDMA (N,N-dimethyl formamide dimethyl acetal) (13.9 g, 117 mmol), and the mixture was heated under reflux. The reaction mixture was extracted with EA, and the extract was washed twice with brine, dried over MgSO$_4$, filtered and evaporated under reduced pressure to remove solvent. The mixture was purified via column chromatography (MC/MeOH=10/1) to obtain 1-[3-(cyclopropylmethoxy)-4-(difluoromethoxy)phenyl]-3-(dimethylamino)prop-2-en-1-one (11 g, 92%).

$^1$H NMR (500 MHz, CDCl$_3$) δ 7.79 (1H, d, J=12.3 Hz, —CH=), 7.56 (1H, s, Ar), 7.43 (1H, m, Ar), 7.15 (1H, d, 7=8.3 Hz, Ar), 6.69 (1H, t, 7=74.6 Hz, —CHF$_2$), 5.65 (1H, d, J=12.5 Hz, =CH—), 3.94 (2H, d, J=6.9 Hz, —OCH$_2$—), 3.15 (3H, s, —NCH$_3$), 2.94 (3H, s, —NCH$_3$), 1.29 (1H, m, —CH—), 0.63 (2H, m, —CH$_2$—), 0.35 (2H, m, —CH$_2$—).

PREPARATION EXAMPLE 2

Preparation of 5-(pyridin-3-yl)-2H-[1,2,4]triazol-3-amine

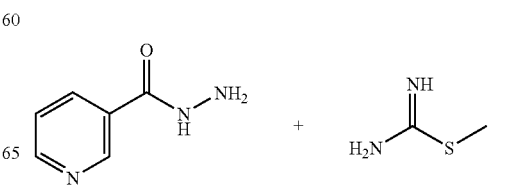

-continued

·H₂SO₄ →

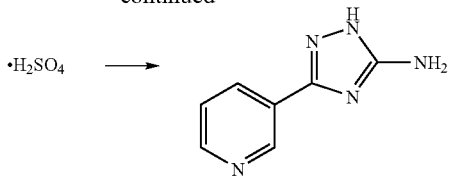

Nicotinic acid hydrazide (10.0 g, 72.92 mmol) was dissolved in aq. NaOH (4.38 g, 109.38 mmol), and 2-methyl-2-thiopseudourea sulfate (12.16 g, 87.50 mmol) was slowly added thereto. The resultant mixture was stirred at room temperature. The reaction mixture was filtered, washed with water and Et₂O, and dried. The solid obtained was heated to 230° C. to obtain the desired compound, 5-(pyridin-3-yl)-2H-[1,2,4]triazol-3-amine (9.2 g, 78%).

$^1$H NMR (300 MHz, DMSO-$d_6$) δ 12.23 (1H, s, NH), 9.06 (1H, m, Ar), 8.53 (1H, m, Ar), 8.19 (1H, m, Ar), 7.42 (1H, m, Ar), 6.20 (2H, s, NH₂).

[Example] Representative Process for Preparing Compound of Chemical Formula (1)

To acetic acid, added were 3-(dimethylamino)-1-(3,4-dialkoxyphenyl)propenone (5) or 3-(3,4-dialkoxyphenyl)-3-oxopropionaldehyde (6) (17.99 mmol) and 3-amino-triazole (4) (26.98 mmol), and the mixture was stirred at ambient temperature. To the reaction mixture, saturated aqueous NaHCO₃ solution was added, and the resultant mixture was extracted three times with ethyl acetate. The organic layer was washed twice with brine, dried over MgSO₄, filtered, and evaporated under reduced pressure to remove the solvent. The mixture was purified via silica gel column chromatography to obtain the desired compound (Chemical Formula 1). The structure of individual compounds represented by Chemical Formula 1 and $^1$H NMR data thereof are listed in Table 1.

EXAMPLE 1

Preparation of 7-[3-(cyclopropylmethoxy)-4-(difluoromethoxy)phenyl]-2-pyridin-3-yl-[1,2,4]triazolo[1,5-a]pyrimidine (Compound 101)

In acetic acid, dissolved was 1-[3-(cyclopropylmethoxy)-4-(difluoromethoxy)phenyl]-3-(dimethylamino)prop-2-en-1-one (5.6 g, 17.99 mmol), and 5-(pyridin-3-yl)-2H-[1,2,4]triazol-3-amine (4.35 g, 26.98 mmol) was added thereto, and the mixture was stirred at ambient temperature for 12 hours.

To the reaction mixture, added was NaHCO₃ (aq), and the resultant mixture was extracted three times with EA, and the extract was washed twice with brine, dried over MgSO₄, filtered and evaporated under reduced pressure to remove solvent. The mixture was purified via silica gel column chromatography (CH₂Cl₂/MeOH, 100/1) to obtain the desired compound, 7-[3-(cyclopropylmethoxy)-4-(difluoromethoxy)phenyl]-2-pyridin-3-yl-[1,2,4]triazolo[1,5-a]pyrimidine (Compound 101) (6.40 g, 87%).

$^1$H NMR (300 MHz, CDCl₃) δ 9.54 (1H, s, Ar), 8.86 (1H, d, J=4.8 Hz, Ar), 8.74 (1H, d, J=4.95 Hz, Ar), 8.60 (1H, d, J=9.7 Hz, Ar), 8.04 (1H, s, Ar), 7.71~7.67 (1H, m, Ar), 7.45~7.39 (2H, m, Ar), 7.25 (1H, m, Ar), 6.80 (1H, t, 7=74.7 Hz, —CHF₂), 4.04 (2H, d, J=6.9 Hz, —OCH₂—), 1.46~1.39 (1H, m, —CH—), 0.73 (2H, m, —CH₂—), 0.43 (2H, m, —CH₂—).

EXAMPLE 2

Preparation of 3-[7-{3-(cyclopropylmethoxy)-4-(difluoromethoxy)phenyl}-[1,2,4]triazolo[1,5-a]pyrimidine-2-yl]-pyridine-N-oxide (Compound 102)

In CH₂Cl₂, dissolved was 7-[3-(cyclopropylmethoxy)-4-(difluoromethoxy)phenyl]-2-pyridin-3-yl-[1,2,4]triazolo[1,5-a]pyrimidine (Compound 101) (3.3 g, 8.06 mmol), and m-chloroperoxybenzoic acid (3.0 g, 12.09 mmol) was slowly added thereto. The mixture was stirred at room temperature. To the reaction mixture, NaHCO₃ (aq) was added, and the resultant mixture was extracted three times with CH₂Cl₂. The extract was washed twice with brine, dried over MgSO₄, filtered, and evaporated under reduced pressure to remove solvent. The mixture was purified via silica gel column chromatography (CH₂Cl₂/MeOH, 50/1) to obtain 3-[7-{3-(cyclopropylmethoxy)-4-(difluoromethoxy)phenyl}-[1,2,4]triazolo[1,5-a]pyri midine-2-yl]-pyridine-N-oxide (Compound 102) (2.7 g, 79%).

$^1$H NMR (200 MHz, CDCl₃) δ 9.14 (1H, s, Ar), 8.90 (1H, d, J=4.6 Hz, Ar), 8.32 (1H, d, J=8.2 Hz, Ar), 8.22 (1H, d, J=8.2 Hz, Ar), 7.84 (1H, s, Ar), 7.72 (1H, d, J=8.4 Hz, Ar), 7.47~7.39 (2H, m, Ar), 7.30~7.27 (1H, m, Ar), 6.81 (1H, t, J=74.4 Hz, —CHF₂), 4.02 (2H, d, J=6.8 Hz, —OCH₂—), 1.39 (1H, m, —CH—), 0.74 (2H, m, —CH₂—), 0.70 (2H, m, —CH₂—).

EXAMPLE 3

Preparation of 2-(6-chloropyridin-3-yl)-7-[3-(cyclopropylmethoxy)-4-(difluoromethoxy)phenyl]-[1,2,4]triazolo[1,5-a]pyrimidine (Compound 104) and 2-(2-chloropyridin-3-yl)-7-[3-(cyclopropylmethoxy)-4-(difluoromethoxy)phenyl]-[1,2,4]triazolo[1,5-a]pyrimidine (Compound 105)

In POCl₃, dissolved was 3-[7-{3-(Cyclopropylmethoxy)-4-(difluoromethoxy)phenyl}-[1,2,4]triazolo[1,5-a]pyri midine-2-yl]-pyridine-N-oxide (Compound 102) (2.7 g, 6.347 mmol), and the mixture was heated under reflux. The solvent was distilled under reduced pressure, and NaHCO₃ (aq.) was added to the residue. The mixture was extracted three times with EA, and the extract was washed twice with brine, dried over MgSO₄, filtered and evaporated under reduced pressure to remove solvent. The mixture was purified via silica gel column chromatography (hexane/EA, 1/1) to obtain the desired compound, 2-(6-chloropyridin-3-yl)-7-[3-(cyclopropylmethoxy)-4-(difluoromethoxy)phenyl]-[1,2,4]triazolo[1,5-a]pyrimidine (Compound 104) (0.07 g, 30%) and 2-(2-chloropyridin-3-yl)-7-[3-(cyclopropylmethoxy)-4-(difluoromethoxy)phenyl]-[1,2,4]triazolo[1,5-a]pyrimidine (Compound 105) (0.09 g, 38%)

Compound 104: $^1$H NMR (200 MHz, CDCl₃) δ 9.33~9.31 (1H, m, Ar), 8.87 (1H, d, J=5.0 Hz, Ar), 8.60~8.55 (1H, m, Ar), 7.98 (1H, d, J=2.0 Hz, Ar), 7.70~7.65 (1H, m, Ar), 7.50~7.39 (2H, m, Ar), 7.25 (1H, d, J=4.4 Hz, Ar), 6.80 (1H, t, J=74.6 Hz, —CHF₂), 4.02 (2H, d, J=6.8 Hz, —OCH₂—), 1.44~1.34 (1H, m, —CH—), 0.76~0.67 (2H, m, —CH₂—), 0.46~0.38 (2H, m, —CH₂—).

Compound 105: $^1$H NMR (200 MHz, CDCl₃) δ 8.91 (1H, d, J=4.8 Hz, Ar), 8.66~8.61 (1H, m, Ar), 8.55~8.52 (1H, m, Ar), 8.24 (1H, d, J=2.0 Hz, Ar), 7.69~7.66 (1H, m, Ar), 7.47~7.25 (3H, m, Ar), 6.80 (1H, t, J=75.0 Hz, —CHF₂), 4.04

(2H, d, J=7.0 Hz, —OCH$_2$—), 1.42~1.29 (1H, m, —CH—), 0.74~0.64 (2H, m, —CH$_2$—), 0.45~0.37 (2H, m, —OCH$_2$—).

EXAMPLE 4

Preparation of 3-[7-{3-(cyclopropylmethoxy)-4-(difluoromethoxy)phenyl}-[1,2,4]triazolo[1,5-a]pyrimidin-2-yl]-pyridinium bisulfate Compound 111)

In methylene chloride, dissolved was 7-[3-(cyclopropylmethoxy)-4-(difluoromethoxy)phenyl]-2-pyridin-3-yl-[1,2,4]triazolo[1,5-a]pyrimidine (Compound 101) (0.03 g, 0.73 mmol), and 95% sulfuric acid (0.008 g, 0.08 mmol) was added thereto. The mixture was stirred at room temperature for 1 hour. When the reaction was completed, the solid produced was filtered, washed with Et$_2$O, and dried to obtain the desired compound, 3-[7-{3-(cyclopropylmethoxy)-4-(difluoromethoxy)phenyl}-[1,2,4]triazolo[1,5-a]pyrimidin-2-yl]-pyridinium bisulfate (Compound 111) (0.024 g, 64.7%).
$^1$H NMR (300 MHz, DMSO-d$_6$) δ 9.44 (1H, d, J=1.5 Hz, Ar), 8.99 (1H, d, J=4.8 Hz, Ar), 8.82~8.80 (1H, m, Ar), 8.71~8.67 (1H, m, Ar), 8.75 (1H, d, J=2.1 Hz, Ar), 7.96~7.93 (1H, m, Ar), 7.77~7.73 (2H, m, Ar), 7.47 (1H, d, J=8.4 Hz, Ar), 7.30 (1H, t, J=75.1 Hz, —CHF$_2$—), 4.06 (2H, d, J=6.9 Hz, —OCH$_2$—), 1.40~1.35 (1H, m, —CH—), 0.65~0.59 (2H, m, —CH$_2$—), 0.41~0.36 (2H, m, —CH$_2$—).

EXAMPLE 5

Preparation of 3-[7-{3-(cyclopropylmethoxy)-4-(difluoromethoxy)phenyl}-[1,2,4]triazolo[1,5-a]pyrimidin-2-yl]-pyridinium chloride (Compound 112)

In tetrahydrofuran, dissolved was 7-[3-(cyclopropylmethoxy)-(difluoromethoxy)phenyl]-2-pyridin-3-yl-[1,2,4]triazolo[1,5-a]pyrimidine (Compound 101) (0.03 g, 0.73 mmol), and the mixture was stirred at room temperature for 1 hour while adding hydrogen chloride gas thereto.
When the reaction was completed, the solid produced was filtered with tetrahydrofuran, and washed with Et$_2$O. The solid was dried, dissolved in EtOH and recrystallized to obtain the desired compound, 3-[7-{3-(cyclopropylmethoxy)-4-(difluoromethoxy)phenyl}-[1,2,4]triazolo[1,5-a]pyrimidin-2-yl]-pyridinium chloride (Compound 112) (0.030 g, 93.6%).
$^1$H NMR (300 MHz, MeOH-d$_4$) δ 9.61 (1H, d, J=7.8 Hz, Ar), 9.34 (1H, d, J=8.1 Hz, Ar), 8.99~8.97 (2H, m, Ar), 8.22~8.20 (1H, m, Ar), 7.99~7.87 (2H, m, Ar), 7.65~7.59 (1H, m, Ar), 7.43 (1H, d, J=8.4 Hz, Ar), 6.98 (1H, t, J=75.0 Hz, —CHF$_2$), 4.07 (2H, d, J=6.9 Hz, —OCH$_2$—), 1.42~1.36 (1H, m, —CH—), 0.70~0.64 (2H, m, —CH$_2$—), 0.45~0.40 (2H, m, —CH$_2$—).

EXAMPLE 6

Preparation of 4-[7-{3-(cyclopropylmethoxy)-4-(difluoromethoxy)phenyl}-[1,2,4]triazolo[1,5-a]pyrimidin-2-yl]benzoic acid (Compound 118)

In aqueous EtOH, dissolved was 4-[7-{3-(cyclopropylmethoxy)-4-(difluoromethoxy)phenyl}-[1,2,4]triazolo[1,5-a]pyrimidin-2-yl]benzonitrile (0.1 g, 0.23 mmol), and NaOH (0.02 g, 0.57 mmol) was added thereto. The mixture was stirred at 120° C. for 12 hours. The reaction mixture was chilled to 0° C. by using ice water, and pH was adjusted to 3~4 by using HCl. The mixture was extracted three times with EA, and the extract was washed three times with brine, dried over MgSO$_4$, and evaporated under reduced pressure to remove solvent. The mixture was purified via silica gel column chromatography (methylene chloride/methanol, 20/1) to obtain the desired compound, 4-[7-{3-(cyclopropylmethoxy)-4-(difluoromethoxy)phenyl}-[1,2,4]triazolo[1,5-a]pyrimidin-2-yl]benzoic acid (Compound 118) (0.04 g, 38%).
$^1$H NMR (300 MHz, CDCl$_3$) δ 8.79 (1H, d, J=4.5 Hz, Ar), 8.32 (2H, d, J=8.4 Hz, Ar), 7.96~7.90 (3H, m, Ar), 7.67~7.63 (1H, m, Ar), 7.35 (1H, d, J=8.4 Hz, Ar), 7.23 (1H, d, J=4.8 Hz, Ar), 6.74 (1H, t, J=74.7 Hz, —CHF$_2$—), 3.97 (2H, d, J=6.9 Hz, —OCH$_2$—), 1.39~1.31 (1H, m, —CH—), 0.68~0.61 (2H, m, —CH$_2$—), 0.38~0.33 (2H, m, —CH$_2$—).

EXAMPLE 7

Preparation of 2-(3-Aminophenyl)-7-[3-(cyclopropylmethoxy)-4-(difluoromethoxy)phenyl]-[1,2,4]triazolo[1,5-a]pyrimidine (Compound 119)

In EtOH, dissolved was 7-[3-(cyclopropylmethoxy)-(difluoromethoxy)phenyl]-2-(3-nitrophenyl)-[1,2,4]triazolo[1,5-a]pyrimidine (0.02 g, 0.04 mmol), and Pd/C was added in a small amount. The mixture was stirred at ambient temperature for 3 hours under H2 (g) atmosphere. After filtering Pd/C off, and the filtrate was extracted three times with ethyl acetate, and the extract was washed twice with brine, dried over MgSO$_4$, and evaporated under reduced pressure to remove solvent. The mixture was purified via silica gel column chromatography (methylene chloride/methanol, 30/1) to obtain the desired compound, 2-(3-aminophenyl)-7-[3-(cyclopropylmethoxy)-4-(difluoromethoxy)phenyl]-[1,2,4]triazolo[1,5-a]pyrimidine (Compound 119) (0.089 g, 42%).
$^1$H NMR (300 MHz, CDCl$_3$) δ 8.81 (1H, d, J=4.8 Hz, Ar), 8.07~8.05 (2H, m, Ar), 7.91 (1H, d, J=7.5 Hz, Ar), 7.69~7.66 (1H, m, Ar), 7.48~7.35 (2H, m, Ar), 7.20 (1H, d, J=4.8 Hz, Ar), 7.37~7.03 (1H, m, Ar), 6.78 (1H, t, J=75.0 Hz, —CHF$_2$—), 4.02 (2H, d, J=6.9 Hz, —OCH$_2$—), 1.45~1.34 (1H, m, —CH—), 0.73~0.64 (2H, m, —CH$_2$—), 0.44~0.39 (2H, m, —CH$_2$—).

EXAMPLE 8

Preparation of 2-(2-cyano-pyridin-5-yl)-7-[3-(cyclopropylmethoxy)-4-(difluoromethoxy)phenyl]-[1,2,4]triazolo[1,5-a]pyrimidine (Compound 123) and 2-(6-cyano-pyridin-5-yl)-7-[3-(cyclopropylmethoxy)-4-(difluoromethoxy)phenyl]-[1,2,4]triazolo[1,5-a]pyrimidine (Compound 124)

In CH$_3$CN, dissolved was 3-[7-{3-(cyclopropylmethoxy)-4-(difluoromethoxy)phenyl}-[1,2,4]triazolo[1,5-a]pyrimidine-2-yl]-pyridine-N-oxide (Compound 102) (0.5 g, 1.17 mmol). While stirring the solution, Et$_3$N (0.2 g, 2.0 mmol) and TMSCN (0.47 g, 4.70 mmol) were slowly added dropwise thereto, and the resultant mixture was heated under reflux. The solvent was distilled under reduced pressure, and NaHCO$_3$(aq) was added to the residue. The mixture was extracted three times with CH$_2$Cl$_2$, and the extract was washed twice with brine, dried over MgSO$_4$, filtered, and evaporated under reduced pressure to remove solvent. The mixture was purified via silica gel column chromatography (MC/EA, 2/1) to obtain the desired compound, 2-(2-cyano-pyridin-5-yl)-7-[3-(cyclopropylmethoxy)-4-(difluoromethoxy)phenyl]-[1,2,4]triazolo[1,5-a]pyrimidine (Compound 123) (0.37 g, 72%) and 2-(6-cyano-pyridin-5-yl)-7-[3-

(cyclopropylmethoxy)-4-(difluoromethoxy)phenyl]-[1,2,4]triazolo[1,5-a]pyrimidine (Compound 124) (0.12 g, 24%).

Compound 123: $^1$H NMR (300 MHz, CDCl$_3$) δ 9.64~9.63 (1H, m, Ar), 8.92 (1H, d, J=4.8 Hz, Ar), 8.78~8.75 (1H, m, Ar), 7.92 (1H, d, J=2.1 Hz, Ar), 7.87~7.84 (1H, m, Ar), 7.71~7.67 (1H, m, Ar), 7.42 (1H, d, J=8.4 Hz, Ar), 7.30~7.24 (1H, m, Ar), 6.81 (1H, t, J=74.7 Hz, —CHF$_2$), 4.02 (2H, d, J=6.9 Hz, —OCH$_2$—), 1.44~1.34 (1H, m, —CH—), 0.76~0.67 (2H, m, —CH$_2$—), 0.45~0.39 (2H, m, —CH$_2$—).

Compound 124: $^1$H NMR (300 MHz, CDCl$_3$) δ 8.93 (1H, d, J=4.8 Hz, Ar), 8.85~8.77 (2H, m, Ar), 8.04 (1H, d, J=2.4 Hz, Ar), 7.82~7.79 (1H, m, Ar), 7.73~7.68 (1H, m, Ar), 7.42~7.34 (2H, m, Ar), 6.82 (1H, t, J=75.0 Hz, —CHF$_2$), 4.10 (2H, d, J=6.9 Hz, —OCH$_2$—), 1.40~1.33 (1H, m, —CH—), 0.68~0.64 (2H, m, —CH$_2$—), 0.46~0.40 (2H, m, —CH$_2$—).

Compound 138: $^1$H NMR (300 MHz, CDCl$_3$) δ 9.67 (1H, d, J=2.1 Hz, Ar), 8.90 (1H, d, J=4.8 Hz, Ar), 8.77 (1H, m, Ar), 8.29 (1H, d, J=8.1 Hz, Ar), 8.01 (1H, d, J=1.8 Hz, Ar), 7.66 (1H, m, Ar), 7.42 (1H, d, J=8.4 Hz, Ar), 7.28 (1H, d, J=4.8 Hz, Ar), 6.81 (1H, t, J=74.7 Hz, —CHF$_2$), 4.06 (3H, s, —COOCH$_3$), 4.02 (2H, d, J=6.9 Hz, —OCH$_2$—), 1.46~1.33 (1H, m, —CH—), 0.75~0.69 (2H, m, —CH$_2$—), 0.45~0.40 (2H, m, —CH$_2$—).

Compound 139: $^1$H NMR (300 MHz, DMSO-d$_6$) δ 9.41 (1H, d, J=1.2 Hz, Ar), 9.00 (1H, d, J=4.8 Hz, Ar), 8.71 (1H, m, Ar), 8.23 (1H, d, J=8.1 Hz, Ar), 8.06 (1H, d, J=2.1 Hz, Ar), 7.95 (1H, m, Ar), 7.74 (1H, d, J=4.5 Hz, Ar), 7.48 (1H, d, J=8.4 Hz, Ar), 7.32 (1H, t, J=74.1 Hz, —CHF$_2$), 4.07 (2H, d, J=6.9 Hz, —OCH$_2$—), 1.44~1.33 (1H, m, —CH—), 0.66~0.60 (2H, m, —CH$_2$—), 0.42~0.37 (2H, m, —CH$_2$—).

EXAMPLE 9

Preparation of 5-[7-{3-(cyclopropylmethoxy)-4-(difluoromethoxy)phenyl}-[1,2,4]triazolo[1,5-a]pyrimidin-2-yl]pyridine-2-carboxylic acid methyl ester (Compound 138) and 5-[7-{3-(cyclopropylmethoxy)-4-(difluoromethoxy)phenyl}-[1,2,4]triazolo[1,5-a]pyrimidin-2-yl]pyridine-2-carboxamide (Compound 139)

In EtOH (13 ml, 220 mmol), dissolved was 2-(2-cyanopyridin-5-yl)-7-[3-(cyclopropylmethoxy)-4-(difluoromethoxy)phenyl]-[1,2,4]triazolo[1,5-a]pyrimidine (Compound 123) (0.12 g, 0.28 mmol), and TMSCl (14 ml, 110 mmol) was slowly added dropwise thereto, and the mixture was stirred at 50° C. To the reaction mixture, NaHCO$_3$(aq) was added, and the mixture was extracted three times with CH$_2$Cl. The extract was washed twice with brine, dried over MgSO$_4$, filtered, and evaporated under reduced pressure to remove solvent. The mixture was purified via silica gel column chromatography (CH$_2$Cl$_2$/MeOH, 100/1) to obtain the desired compound, 5-[7-{3-(cyclopropylmethoxy)-4-(difluoromethoxy)phenyl}-[1,2,4]triazolo[1,5-a]pyrimidin-2-yl]pyridine-2-carboxylic acid methyl ester (Compound 138) (0.05 g, 40%) and 5-[7-{3-(cyclopropylmethoxy)-4-(difluoromethoxy)phenyl}-[1,2,4]triazolo[1,5-a]pyrimidin-2-yl]pyridine-2-carboxamide (Compound 139) (0.03 g, 24%).

EXAMPLE 10

Preparation of 5-[7-{3-(cyclopropylmethoxy)-4-(difluoromethoxy)phenyl}-[1,2,4]triazolo[1,5-a]pyrimidin-2-yl]pyridine-2-carboxylic acid (Compound 137)

In aqueous MeOH, dissolved was 5-[7-{3-(cyclopropylmethoxy)-4-(difluoromethoxy)phenyl}-[1,2,4]triazolo[1,5-a]pyrimidin-2-yl]pyridine-2-carboxylic acid methyl ester (Compound 138) (0.05 g, 0.11 mmol), and LiOH (0.013 g, 0.32 mmol) was slowly added thereto. By using dilute HCl, pH of the reaction mixture was adjusted to 4~5. The mixture was extracted three times with EA, and the extract was washed twice with brine, dried over MgSO$_4$, filtered, and evaporated under reduced pressure to remove solvent. The mixture was purified via silica gel column chromatography (MeOH) to obtain desired compound, 5-[7-{3-(cyclopropylmethoxy)-4-(difluoromethoxy)phenyl}-[1,2,4]triazolo[1,5-a]pyrimidin-2-yl]pyridine-2-carboxylic acid (Compound 137) (0.017 g, 35%).

$^1$H NMR (300 MHz, CD$_3$OD) δ 9.43 (1H, s, Ar), 8.90 (1H, m, Ar), 8.68 (1H, m, Ar), 8.20 (1H, s, Ar), 8.08 (1H, s, Ar), 7.87 (1H, m, Ar), 7.57 (1H, m, Ar), 7.40 (1H, m, Ar), 6.98 (1H, t, J=75.0 Hz, —CHF$_2$), 4.06 (2H, d, J=6.9 Hz, —OCH$_2$—), 1.40~1.32 (1H, m, —CH—), 0.69~0.64 (2H, m, —CH$_2$—), 0.46~0.42 (2H, m, —CH$_2$—).

Table 1

TABLE 1

| | IUPAC name | $^1$H NMR |
|---|---|---|
| 101 | 7-[3-(Cyclopropylmethoxy)-4-(difluoromethoxy)phenyl]-2-pyridin-3-yl-[1,2,4]triazolo[1,5-a]pyrimidine | $^1$H NMR (300 MHz, CDCl$_3$) δ 9.54 (1H, s, Ar), 8.86 (1H, d, J = 4.8 Hz, Ar), 8.74 (1H, d, J = 4.95 Hz, Ar), 8.60 (1H, d, J = 9.7 Hz, Ar), 8.04 (1H, s, Ar), 7.71~7.67 (1H, m, Ar), 7.45~7.39 (2H, m, Ar), 7.25 (1H, m, Ar), 6.80 (1H, t, J = 74.7 Hz, —CHF$_2$), 4.04 (2H, d, J = 6.9 Hz, —OCH$_2$—), 1.46~1.39 (1H, m, —CH—), 0.73 (2H, m, —CH$_2$—), 0.43 (2H, m, —CH$_2$—). |
| 102 | 3-[7-{3-(Cyclopropylmethoxy)-4-(difluoromethoxy)phenyl}-[1,2,4]triazolo[1,5-a]pyrimidine-2-yl]-pyridine-N-oxide | $^1$H NMR (200 MHz, CDCl$_3$) δ 9.14 (1H, s, Ar) 8.90 (1H, d, J = 4.6 Hz, Ar), 8.32 (1H, d, J = 8.2 Hz, Ar), 8.22 (1H, d, J = 8.2 Hz, Ar), 7.84 (1H, s, Ar), 7.72 (1H, d, J = 8.4 Hz, Ar), 7.47~7.39 (2H, m, Ar), 7.30~7.27 (1H, m, Ar), 6.81 (1H, t, J = 74.4 Hz, —CHF$_2$), 4.02 (2H, d, J = 6.8 Hz, —OCH$_2$—), 1.39 (1H, m, —CH—), 0.74 (2H, m, —CH$_2$—), 0.70 (2H, m, —CH$_2$—). |
| 103 | 7-[3-(Cyclopropylmethoxy)-4-(difluoromethoxy)phenyl]-2-pyridin-4-yl-[1,2,4]triazolo[1,5-a]pyrimidine | $^1$H NMR (200 MHz, CDCl$_3$) δ 8.90~8.77 (3H, m, Ar), 8.21~8.18 (2H, m, Ar), 7.99 (1H, d, J = 2 Hz, Ar), 7.23~7.68 (1H, m, Ar), 7.41 (1H, d, J = 8.6 Hz, Ar), 7.28~7.25 (1H, m, Ar), 6.80 (1H, t, J = 74.4 Hz, —CHF$_2$), 4.04 (2H, d, J = 7.0 Hz, —OCH$_2$—), 1.50~1.35 (1H, m, —CH—), 0.77~0.70 (2H, m, —CH$_2$—), 0.47~0.39 (2H, m, —CH$_2$—). |
| 104 | 2-(2-Chloro-pyridin-5-yl)-7-[3-(cyclopropylmethoxy)- | $^1$H NMR (200 MHz, CDCl$_3$) δ 9.33~9.31 (1H, m, Ar), 8.87 (1H, d, J = 5.0 Hz, Ar), 8.60~8.55 (1H, m, Ar), |

TABLE 1-continued

| | IUPAC name | $^1$H NMR |
|---|---|---|
| | 4-(difluoromethoxy)phenyl]-[1,2,4]triazolo[1,5-a]pyrimidine | 7.98 (1H, d, J = 2.0 Hz, Ar), 7.70~7.65 (1H, m, Ar), 7.50~7.39 (2H, m, Ar), 7.25 (1H, d, J = 4.4 Hz, Ar), 6.80 (1H, t, J = 74.6 Hz, —CHF$_2$), 4.02 (2H, d, J = 6.8 Hz, —OCH$_2$—), 1.44~1.34 (1H, m, —CH—), 0.76~0.67 (2H, m, —CH$_2$—), 0.46~0.38 (2H, m, —CH$_2$—). |
| 105 | 2-(2-Chloro-pyridin-3-yl)-7-[3-(cyclopropylmethoxy)-4-(difluoromethoxy)phenyl]-[1,2,4]triazolo[1,5-a]pyrimidine | $^1$H NMR (200 MHz, CDCl$_3$) δ 8.91 (1H, d, J = 4.8 Hz, Ar), 8.66~8.61 (1H, m, Ar), 8.55~8.52 (1H, m, Ar), 8.24 (1H, d, J = 2.0 Hz, Ar), 7.69~7.66 (1H, m, Ar), 7.47~7.25 (3H, m, Ar), 6.80 (1H, t, J = 75.0 Hz, —CHF$_2$), 4.04 (2H, d, J = 7.0 Hz, —OCH$_2$—), 1.42~1.29 (1H, m, —CH—), 0.74~0.64 (2H, m, —CH$_2$—), 0.45~0.37 (2H, m, —CH$_2$—). |
| 106 | 7-[3-(Cyclopropylmethoxy)-4-(difluoromethoxy)phenyl]-2-(3-fluorophenyl)-[1,2,4]triazolo[1,5-a]pyrimidine | $^1$H NMR (300 MHz, CDCl$_3$) δ 8.85 (1H, d, J = 4.8 Hz, Ar), 8.81~8.01 (3H, m, Ar), 7.70~7.67 (1H, m, Ar), 7.51~7.39 (2H, m, Ar), 7.26~7.24 (2H, m, Ar), 6.79 (1H, t, J = 75.0 Hz, —CHF$_2$), 4.04 (2H, d, J = 6.9 Hz, —OCH$_2$—), 1.48~1.25 (1H, m, —CH—), 0.75~0.69 (2H, m, —CH$_3$), 0.46~0.40 (2H, m, —CH$_2$—). |
| 107 | 7-[3-(Cyclopropylmethoxy)-4-(difluoromethoxy)phenyl]-2-(3-methoxyphenyl)-[1,2,4]triazolo[1,5-a]pyrimidine | $^1$H NMR (300 MHz, CDCl$_3$) δ 8.83 (1H, d, J = 4.8 Hz, Ar), 8.11 (1H, d, J = 2.1 Hz, Ar), 7.93~7.91 (2H, m, Ar), 7.70~7.67 (1H, m, Ar), 7.43~7.38 (2H, m, Ar), 7.26~7.22 (1H, m, Ar), 6.72 (1H, t, J = 74.7 Hz, —CHF$_2$), 4.04 (2H, d, J = 6.9 Hz, —OCH$_2$—), 3.91 (3H, s, OCH$_3$), 1.28~1.23 (1H, m, —CH—), 0.72~0.68 (2H, m, —CH$_2$—), 0.45~0.41 (2H, m, —CH$_2$—). |
| 108 | 3-[7-{3-(Cyclopropylmethoxy)-4-(difluoromethoxy)phenyl}-[1,2,4]triazolo[1,5-a]pyrimidine-2-yl]-6-Chloropyridine-N-oxide | $^1$H NMR (300 MHz, CDCl3) δ 9.28 (1H, m, Ar), 8.90 (1H, d, J = 4.8 Hz, Ar), 8.17~8.13 (1H, m, Ar), 7.83 (1H, d, J = 2.1 Hz, Ar), 7.72~7.63 (2H, m, Ar), 7.42 (1H, d, J = 8.4 Hz, Ar), 7.29~7.27 (1H, m, Ar), 6.80 (1H, t, J = 74.7 Hz, —CHF$_2$), 4.01 (2H, d, J = 6.9 Hz, —OCH$_2$—), 1.44~1.25 (1H, m, —CH—), 0.76~0.65 (2H, m, —CH$_2$—), 0.46~0.41 (2H, m, —CH$_2$—). |
| 109 | 3-[7-{3-(Cyclopropylmethoxy)-4-(difluoromethoxy)phenyl}-[1,2,4]triazolo[1,5-a]pyrimidine-2-yl]-2-Chloropyridine-N-oxide | $^1$H NMR (300 MHz, CDCl$_3$—) δ 8.94 (1H, d, J = 4.8 Hz, Ar), 8.52~8.50 (1H, m, Ar), 8.21~8.17 (1H, m, Ar), 8.09 (1H, d, J = 2.4 Hz, Ar), 7.69~7.65 (1H, m, Ar), 7.41~7.33 (3H, m, Ar), 6.80 (1H, t, J = 74.7 Hz, —CHF$_2$), 4.01 (2H, d, J = 6.9 Hz, —OCH$_2$—), 1.38~1.33 (1H, m, —CH—), 0.71~0.66 (2H, m, —CH$_2$—), 0.43~0.40 (2H, m, —CH$_2$—). |
| 110 | 4-[7-{3-(Cyclopropylmethoxy)-4-(difluoromethoxy)phenyl}-[1,2,4]triazolo[1,5-a]pyrimidine-2-yl]-pyridine-N-oxide | $^1$H NMR (300 MHz, CDCl$_3$) δ 8.88 (1H, d, J = 4.5 Hz, Ar), 8.32~8.28 (2H, m, Ar), 8.23~8.20 (2H, m, Ar), 7.85 (1H, d, J = 1.8 Hz, Ar), 7.72~7.69 (1H, m, Ar), 7.42 (1H, d, J = 8.4 Hz, Ar), 7.27~7.25 (1H, m, Ar), 6.80 (1H, t, J = 74.4 Hz, —CHF$_2$), 4.01 (2H, d, J = 6.9 Hz, —OCH$_2$—), 1.44~1.35 (1H, m, —CH—), 0.74~0.68 (2H, m, —CH$_2$—), 0.44~0.39 (2H, m, —CH$_2$—). |
| 111 | 3-[7-{3-(Cyclopropylmethoxy)-4-(difluoromethoxy)phenyl}-[1,2,4]triazolo[1,5-a]pyrimidin-2-yl]-pyridinium bisulfate | $^1$H NMR (300 MHz, DMSO-d$_6$) δ 9.44 (1H, d, J = 1.5 Hz, Ar), 8.99 (1H, d, J = 4.8 Hz, Ar), 8.82~8.80 (1H, m, Ar), 8.71~8.67 (1H, m, Ar,) 8.75 (1H, d, J = 2.1 Hz, Ar), 7.96~7.93 (1H, m, Ar), 7.77~7.73 (2H, m, Ar), 7.47 (1H, d, J = 8.4 Hz, Ar), 7.30 (1H, t, J = 75.1 Hz, —CHF$_2$), 4.06 (2H, d, J = 6.9 Hz, —OCH$_2$—), 1.40~1.35 (1H, m, —CH—), 0.65~0.59 (2H, m, —CH$_2$—), 0.41~0.36 (2H, m, —CH$_2$—). |
| 112 | 3-[7-{3-(Cyclopropylmethoxy)-4-(difluoromethoxy)phenyl}-[1,2,4]triazolo[1,5-a]pyrimidin-2-yl]-pyridinium chloride | $^1$H NMR (300 MHz, CD$_3$OD) δ 9.61 (1H, d, J = 7.8 Hz, Ar), 9.34 (1H, d, J = 8.1 Hz, Ar), 8.99~8.97 (1H, m, Ar), 8.22~8.20 (1H, m, Ar), 7.99~7.87 (2H, m, Ar), 7.65~7.59 (1H, m, Ar), 7.43 (1H, d, J = 8.4 Hz, Ar), 6.98 (1H, t, J = 75.0 Hz, —CHF$_2$), 4.07 (2H, d, J = 6.9 Hz, —OCH$_2$—), 1.42~1.36 (1H, m, —CH—), 0.70~0.64 (2H, m, —CH$_2$—), 0.45~0.40 (2H, m, —CH$_2$—). |
| 113 | 7-[3-(Cyclopropylmethoxy)-4-(difluoromethoxy)phenyl]-2-p-tolyl-[1,2,4]triazolo[1,5-a]pyrimidine | $^1$H NMR (300 MHz, CDCl$_3$) δ 8.78 (1H, d, J = 4.8 Hz, Ar), 8.22 (2H, d, J = 8.1 Hz, Ar), 8.10 (1H, d, J = 2.1 Hz, Ar), 7.69~7.65 (1H, m, Ar), 7.36~7.31 (3H, m, Ar), 7.28~7.23 (1H, m, Ar), 7.17~7.15 (1H, m, Ar), 6.66 (1H, t, J = 74.7 Hz, —CHF$_2$), 4.02 (2H, d, J = 6.9 Hz, —OCH$_2$—), 2.38 (3H, s, —CH$_3$), 1.45~1.40 (1H, m, —CH—), 0.74~0.67 (2H, m, —CH$_2$—), 0.45~0.40 (2H, m, —CH$_2$—). |
| 114 | 7-(3,4-Bis-difluoromethoxyphenyl)-2-pyridin-3-yl[1,2,4]triazolo[1,5-a]pyrimidine | $^1$H NMR (300 MHz, CDCl$_3$) δ 9.58 (1H, m, Ar), 8.90 (1H, m, Ar), 8.76~8.74 (1H, m, Ar), 8.65~8.61 (1H, m, Ar), 8.35 (1H, m, Ar), 8.12~8.08 (1H, m, Ar), 7.54 (1H, m, Ar), 7.48~7.44 (1H, m, Ar), 7.28~7.25 (1H, m, Ar), 6.69 (1H, t, J = 72.6 Hz, —CHF$_2$), 6.68 (1H, t, J = 72.6 Hz, —CHF$_2$). |
| 115 | 2-(3-Cyanophenyl)-7-[3-(cyclopropylmethoxy)-4-(difluoromethoxy)phenyl]- | $^1$H NMR (300 MHz, CDCl$_3$) δ 8.86 (1H, d, J = 4.8 Hz, Ar), 8.84~8.56 (2H, m, Ar), 7.97 (1H, d, J = 1.8 Hz, Ar), 7.79~7.60 (3H, m, Ar), 7.41 (1H, d, J = 3.6 Hz, |

TABLE 1-continued

| | IUPAC name | $^1$H NMR |
|---|---|---|
| | [1,2,4]triazolo[1,5-a]pyrimidine | Ar), 7.27~7.25 (1H, m, Ar), 6.81 (1H, t, J = 75.0 Hz, —CHF$_2$), 4.08 (2H, d, J = 2.7 Hz, —OCH$_2$—), 1.45~1.38 (1H, m, —CH—), 0.76~0.70 (2H, m, —CH$_2$—), 0.47~0.42 (2H, m, —CH$_2$—). |
| 116 | 7-[3-(Cyclopropylmethoxy)-4-(difluoromethoxy)phenyl]-2-(3-nitrophenyl)-[1,2,4]triazolo[1,5-a]pyrimidine | $^1$H NMR (300 MHz, CDCl$_3$) δ 9.10 (1H, d, J = 1.5 Hz, Ar), 8.84 (1H, d, J = 4.5 Hz, Ar), 8.64 (1H, d, J = 7.8 Hz, Ar), 8.32~8.28 (1H, m, Ar), 8.05 (1H, d, J = 2.1 Hz, Ar), 7.69~7.64 (2H, m, Ar), 7.38 (1H, d, J = 8.4 Hz, Ar), 7.27~7.25 (1H, m, Ar), 6.80 (1H, t, J = 75.0 Hz, —CHF$_2$), 4.05 (2H, d, J = 6.9 Hz, —OCH$_2$—), 1.42~1.38 (1H, m, —CH—), 0.73~0.66 (2H, m, —CH$_2$—), 0.45~0.40 (2H, m, —CH$_2$—). |
| 117 | 2-(4-Cyanophenyl)-7-[3-(cyclopropylmethoxy)-4-(difluoromethoxy)phenyl]-[1,2,4]triazolo[1,5-a]pyrimidine | $^1$H NMR (200 MHz, CDCl$_3$) δ 8.88 (1H, d, J = 4.5 Hz, Ar), 8.48~8.45 (2H, m, Ar), 7.94 (1H, d, J = 2.4 Hz, Ar), 7.81~7.69 (3H, m, Ar), 7.41 (1H, d, J = 8.4 Hz, Ar), 7.25 (1H, d, J = 5.1 Hz, Ar), 6.80 (1H, t, J = 75.0 Hz, —CHF$_2$), 4.02 (2H, d, J = 7.2 Hz, —OCH$_2$—), 1.44~1.38 (1H, m, —CH—), 0.74~0.68 (2H, m, —CH$_2$—), 0.44~0.39 (2H, m, —CH$_2$—). |
| 118 | 4-[7-{3-(Cyclopropylmethoxy)-4-(difluoromethoxy)phenyl}-[1,2,4]triazolo[1,5-a]pyrimidin-2-yl]benzoic acid | $^1$H NMR (300 MHz, CDCl$_3$) δ 8.79 (1H, d, J = 4.5 Hz, Ar), 8.32 (2H, d, J = 8.4 Hz, Ar), 7.96~7.90 (3H, m, Ar), 7.67~7.63 (1H, m, Ar), 7.35 (1H, d, J = 8.4 Hz, Ar), 7.23 (1H, d, J = 4.8 Hz, Ar), 6.74 (1H, t, J = 74.7 Hz, —CHF$_2$—), 3.97 (2H, d, J = 6.9 Hz, —OCH$_2$—), 1.39~1.31 (1H, m, —CH—), 0.68~0.61 (2H, m, —CH$_2$—), 0.38~0.33 (2H, m, —CH$_2$—). |
| 119 | 2-(3-Aminophenyl)-7-[3-(cyclopropylmethoxy)-4-(difluoromethoxy)phenyl]-[1,2,4]triazolo[1,5-a]pyrimidine | $^1$H NMR (300 MHz, CDCl$_3$) δ 8.81 (1H, d, J = 4.8 Hz, Ar), 8.07~8.05 (2H, m, Ar), 7.91 (1H, d, J = 7.5 Hz, Ar), 7.69~7.66 (1H, m, Ar), 7.48~7.35 (2H, m, Ar), 7.20 (1H, d, J = 4.8 Hz, Ar), 7.37~7.03 (1H, m, Ar), 6.78 (1H, t, J = 75.0 Hz, —CHF$_2$), 4.02 (2H, d, J = 6.9 Hz, —OCH$_2$—), 1.45~1.34 (1H, m, —CH—), 0.73~0.64 (2H, m, —CH$_2$—), 0.44~0.39 (2H, m, —CH$_2$—). |
| 120 | 2-(3-Chlorophenyl)-7-[3-(cyclopropylmethoxy)-4-(difluoromethoxy)phenyl]-[1,2,4]triazolo[1,5-a]pyrimidine | $^1$H NMR (300 MHz, CDCl$_3$) δ 8.83 (1H, d, J = 4.5 Hz, Ar), 8.30 (1H, d, J = 2.1 Hz, Ar), 8.25~8.22 (1H, m, Ar), 8.08 (1H, d, J = 2.1 Hz, Ar), 7.69~7.65 (1H, m, Ar), 7.46~7.38 (3H, m, Ar), 7.26~7.22 (1H, m, Ar), 6.80 (1H, t, J = 74.7 Hz, —CHF$_2$), 4.05 (2H, d, J = 7.2 Hz, —OCH$_2$—), 1.46~1.41 (1H, m, —CH—), 0.76~0.69 (2H, m, —CH$_2$—), 0.47~0.41 (2H, m, —CH$_2$—). |
| 121 | 2-(3-Bromophenyl)-7-[3-(cyclopropylmethoxy)-4-(difluoromethoxy)phenyl]-[1,2,4]triazolo[1,5-a]pyrimidine | $^1$H NMR (300 MHz, CDCl$_3$) δ 8.84 (1H, d, J = 4.8 Hz, Ar), 8.49~8.48 (1H, m, Ar), 8.30 (1H, d, J = 7.8 Hz, Ar), 8.08 (1H, d, J = 2.1 Hz, Ar), 7.68~7.61 (2H, m, Ar), 7.42~7.35 (1H, m, Ar), 7.26~7.22 (3H, m, Ar), 6.80 (1H, t, J = 74.7 Hz, —CHF$_2$), 4.04 (2H, d, J = 6.9 Hz, —OCH$_2$—), 1.44~1.41 (1H, m, —CH—), 0.88~0.69 (2H, m, —CH$_2$—), 0.47~0.43 (2H, m, —CH$_2$—). |
| 122 | 7-(3,4-Bis-difluoromethoxyphenyl)-2-(3-cyanophenyl)-[1,2,4]triazolo[1,5-a]pyrimidine | $^1$H NMR (300 MHz, CDCl$_3$) δ 8.91 (1H, m, Ar), 8.67 (1H, m, Ar), 8.63~8.59 (1H, m, Ar), 8.30 (1H, m, Ar), 8.13~8.10 (1H, m, Ar), 7.80~7.77 (1H, m, Ar), 7.67~7.55 (2H, m, Ar), 7.29~7.26 (1H, m, Ar), 6.70 (1H, t, J = 72.9 Hz, —CHF$_2$), 6.69 (1H, t, J = 72.6 Hz, —CHF$_2$). |
| 123 | 2-(2-cyanopyridin-5-yl)-7-[3-(cyclopropylmethoxy)-4-(difluoromethoxy)phenyl]-[1,2,4]triazolo[1,5-a]pyrimidine | $^1$H NMR (300 MHz, CDCl$_3$) δ 9.64~9.63 (1H, m, Ar), 8.92 (1H, d, J = 4.8 Hz, Ar), 8.78~8.75 (1H, m, Ar), 7.92 (1H, d, J = 2.1 Hz, Ar), 7.87~7.84 (1H, m, Ar), 7.71~7.67 (1H, m, Ar), 7.42 (1H, d, J = 8.4 Hz, Ar), 7.30~7.24 (1H, m, Ar), 6.81 (1H, t, J = 74.7 Hz, —CHF$_2$), 4.02 (2H, d, J = 6.9 Hz, —OCH$_2$—), 1.44~1.34 (1H, m, —CH—), 0.76~0.67 (2H, m, —CH$_2$—), 0.45~0.39 (2H, m, —CH$_2$—). |
| 124 | 2-(6-cyanopyridin-5-yl)-7-[3-(cyclopropylmethoxy)-4-(difluoromethoxy)phenyl]-[1,2,4]triazolo[1,5-a]pyrimidine | $^1$H NMR (300 MHz, CDCl$_3$) δ 8.93 (1H, d, J = 4.8 Hz, Ar), 8.85~8.77 (2H, m, Ar), 8.04 (1H, d, J = 2.4 Hz, Ar), 7.82~7.79 (1H, m, Ar), 7.73~7.68 (1H, m, Ar), 7.42~7.34 (2H, m, Ar), 6.82 (1H, t, J = 75.0 Hz, —CHF$_2$), 4.10 (2H, d, J = 6.9 Hz, —OCH$_2$—), 1.40~1.33 (1H, m, —CH—), 0.68~0.64 (2H, m, —CH$_2$—), 0.46~0.40 (2H, m, —CH$_2$—). |
| 125 | 7-[3-(Cyclopropylmethoxy)-4-(difluoromethoxy)phenyl]-2-(4-trifluoromethylphenyl)-[1,2,4]triazolo[1,5-a]pyrimidine | $^1$H NMR (300 MHz, CDCl$_3$) δ 8.87 (1H, d, J = 4.5 Hz, Ar), 8.48 (1H, d, J = 7.2 Hz, Ar), 8.01 (1H, m, Ar), 7.78~7.69 (3H, m, Ar), 7.42 (1H, d, J = 8.4 Hz, Ar), 7.25 (1H, m, Ar), 6.81 (1H, t, J = 74.7 Hz, —CHF$_2$), 4.03 (2H, d, J = 7.2 Hz, —OCH$_2$—), 1.50 (1, m, —CH—), 0.75~0.69 (2H, m, —CH$_2$—), 0.46~0.41 (2H, m, —CH$_2$—). |
| 126 | 7-[3-(Cyclopropylmethoxy)-4-(difluoromethoxy)phenyl]-2-(3-iodophenyl)- | $^1$H NMR (300 MHz, CDCl$_3$) δ 8.84 (1H, d, J = 4.5 Hz, Ar), 8.68 (1H, m, Ar), 8.33 (1H, d, J = 7.8 Hz, Ar), 8.08 (1H, m, Ar), 7.84~7.81 (1H, m, Ar), |

TABLE 1-continued

| | IUPAC name | $^1$H NMR |
|---|---|---|
| | [1,2,4]triazolo[1,5-a]pyrimidine | 7.68~7.64 (1H, m, Ar), 7.40 (1H, d, J = 8.4 Hz, Ar), 7.26~7.20 (2H, m, Ar), 6.81 (1H, t, J = 74.7 Hz, —CHF$_2$), 4.05 (2H, d, J = 6.9 Hz, —OCH$_2$—), 1.49~1.39 (1H, m, —CH—), 0.77~0.70 (2H, m, —CH$_2$—), 0.48~0.43 (2H, m, —CH$_2$—). |
| 127 | 7-[3-(Cyclopropylmethoxy)-4-(difluoromethoxy)phenyl]-2-(4-iodophenyl)-[1,2,4]triazolo[1,5-a]pyrimidine | $^1$H NMR (300 MHz, CDCl$_3$) δ 8.83 (1H, d, J = 4.8 Hz, Ar), 8.10~8.02 (3H, m, Ar), 7.87~7.83 (2H, m, Ar), 7.70~7.67 (1H, m, Ar), 7.41 (1H, m, Ar), 7.22 (1H, m, Ar), 6.79 (1H, t, J = 74.4 Hz, —CHF$_2$), 4.02 (2H, d, J = 6.9 Hz, —OCH$_2$—), 1.45~1.40 (1H, m, —CH—), 0.75~0.68 (2H, m, —CH$_2$—), 0.45~0.40 (2H, m, —CH$_2$—). |
| 128 | 7-[3-(Cyclopropylmethoxy)-4-(difluoromethoxy)phenyl]-2-(3-trifluoromethylphenyl)-[1,2,4]triazolo[1,5-a]pyrimidine | $^1$H NMR (300 MHz, CDCl$_3$) δ 8.87~8.86 (1H, m, Ar), 8.61~8.54 (2H, m, Ar), 8.10 (1H, d, J = 2.1 Hz, Ar), 7.77~7.62 (3H, m, Ar), 7.41 (1H, d, J = 8.1 Hz, Ar), 7.25~7.06 (1H, m, Ar), 6.81 (1H, t, J = 75.0 Hz, —CHF$_2$), 4.04 (2H, d, J = 6.9 Hz, —OCH$_2$—), 1.41~1.39 (1H, m, —CH—), 0.74~0.68 (2H, m, —CH$_2$—), 0.45~0.40 (2H, m, —CH$_2$—). |
| 129 | 7-[3-(Cyclopentoxy)-4-methoxyphenyl]-2-(3-cyanophenyl)-[1,2,4]triazolo[1,5-a]pyrimidine | $^1$H NMR (300 MHz, CDCl$_3$) δ 9.04 (1H, m, Ar), 8.80 (1H, m, Ar), 8.61~8.58 (1H, m, Ar), 8.19~8.15 (1H, m, Ar), 8.04 (1H, m, Ar), 7.78~7.75 (1H, m, Ar), 7.62~7.56 (1H, m, Ar), 7.22 (1H, m, Ar), 7.10 (1H, m, Ar), 4.93~4.89 (1H, m, —OCH—), 3.97 (3H, s, —OCH$_3$), 2.11~2.02 (4H, m, —CH$_2$—, —CH$_2$—), 1.95~1.83 (2H, m, —CH$_2$—), 1.73~1.61 (2H, m, —CH$_2$—). |
| 130 | 3-[7-(3,4-Bis-difluoromethoxyphenyl)-[1,2,4]triazolo[1,5-a]pyrimidine-2-yl]-pyridine-N-oxide | $^1$H NMR (300 MHz, CDCl$_3$) δ 9.19 (1H, m, Ar), 8.94 (1H, m, Ar), 8.36~8.10 (4H, m, Ar), 7.55 (1H, m, Ar), 7.48~7.43 (1H, m, Ar), 7.32~7.29 (1H, m, Ar), 6.70 (1H, t, J = 72.6 Hz, —CHF$_2$), 6.68 (1H, t, J = 72.9 Hz, —CHF$_2$). |
| 131 | 3-[7-{3-(Cyclopropylmethoxy)-4-(difluoromethoxy)phenyl}-[1,2,4]triazolo[1,5-a]pyrimidin-2-yl]benzoic acid | $^1$H NMR (300 MHz, CDCl$_3$) δ 8.88 (1H, d, J = 4.5 Hz, Ar), 8.78~8.77 (1H, m, Ar), 8.45~8.41 (1H, m, Ar), 8.10 (1H, d, J = 39.9 Hz, Ar), 8.03~7.99 (1H, m, Ar), 7.89~7.85 (1H, m, Ar), 7.66~7.53 (1H, m, Ar), 7.41 (1H, d, J = 8.7 Hz, Ar), 6.98 (1H, t, J = 75.0 Hz, —CHF$_2$), 4.09 (2H, d, J = 7.2 Hz, —OCH$_2$—), 1.44~1.39 (1H, m, —CH—), 0.70~0.64 (2H, m, —CH$_2$—), 0.46~0.41 (2H, m, —CH$_2$—). |
| 132 | 7-[3-(Cyclopropylmethoxy)-4-(difluromethoxy)phenyl]-2-m-tolyl-[1,2,4]triazolo[1,5-a]pyrimidine | $^1$H NMR (300 MHz, CDCl$_3$), δ 8.81 (1H, d, J = 4.8 Hz, Ar), 7.70~7.67 (1H, m, Ar), 7.41~7.19 (5H, m, Ar), 6.79 (1H, t, J = 74.7 Hz, —CHF$_2$), 4.04 (2H, d, J = 7.2 Hz, —OCH$_2$—), 2.45 (1H, s, —CH$_3$), 1.46~1.41 (1H, m, —CH—), 0.74~0.68 (2H, m, —CH$_2$—), 0.45~0.40 (2H, m, —CH$_2$—). |
| 133 | 7-[3-(Cyclopropylmethoxy)-4-(difluoromethoxy)phenyl]-2-(3,5-dimethylphenyl)-[1,2,4]triazolo[1,5-a]pyrimidine | $^1$H NMR (300 MHz, CDCl$_3$) δ 8.80 (1H, d, J = 4.8 Hz, Ar), 8.10 (1H, d, J = 2.1 Hz, Ar), 7.69 (2H, s, Ar), 7.69~7.47 (1H, m, Ar), 7.66~7.65 (4H, m, Ar), 7.40~7.37 (1H, m, Ar), 7.26~7.13 (3H, m, Ar) 6.79 (1H, t, J = 74.7 Hz, —CHF$_2$), 4.05 (2H, d, J = 6.9 Hz, —OCH$_2$—), 1.46 (6H, s, —CH$_3$, —CH$_3$), 1.45~1.39 (1H, m, —CH—), 0.74~0.68 (2H, m, —CH$_2$—), 0.45~0.40 (2H, m, —CH$_2$—). |
| 134 | 7-[3-(Cyclopropylmethoxy)-4-(difluoromethoxy)phenyl]-2-(3-methoxy-4-methylphenyl)-[1,2,4]triazolo[1,5-a]pyrimidine | $^1$H NMR (300 MHz, CDCl$_3$) δ 8.80 (1H, d, J = 4.8 Hz, Ar), 8.13 (1H, m, Ar), 7.86~7.83 (2H, m, Ar), 7.69~7.66 (1H, m, Ar), 7.39 (1H, m, Ar), 7.27~7.18 (2H, m, Ar), 6.79 (1H, t, J = 74.7 Hz, —CHF$_2$), 4.04 (2H, d, J = 7.2 Hz, —OCH$_2$—), 3.96 (3H, s, —OCH$_3$), 2.30 (3H, s, —CH$_3$), 1.47~1.35 (1H, m, —CH—), 0.74~0.68 (2H, m, —CH$_2$—), 0.44~0.39 (2H, m, —CH$_2$—). |
| 135 | 7-[3-(Cyclopentoxy)-4-methoxyphenyl]-2-(3-pyridyl)-[1,2,4]triazolo[1,5-a]pyrimidine | $^1$H NMR (300 MHz, CDCl$_3$) δ 9.59 (1H, m, Ar), 8.82 (1H, m, Ar), 8.74~8.72 (1H, m, Ar), 8.67~8.63 (1H, m, Ar), 7.99 (1H, m, Ar), 7.80~7.76 (1H, m, Ar), 7.47~7.42 (1H, m, Ar), 7.23 (1H, m, Ar), 7.09 (1H, m, Ar), 4.93~4.88 (1H, m, —OCH—), 3.99 (1H, s, —OCH$_3$), 2.06~2.02 (4H, m, —CH$_2$—, —CH$_2$—), 1.95~1.87 (2H, m, —CH$_2$—), 1.74~1.67 (2H, m, —CH$_2$—). |
| 136 | 7-[3-(Cyclopropylmethoxy)-4-(difluoromethoxy)phenyl]-2-(2,4-dimethylphenyl)-[1,2,4]triazolo[1,5-a]pyrimidine | $^1$H NMR (300 MHz, CDCl$_3$) δ 8.81 (1H, d, J = 4.8 Hz, Ar), 8.20~8.17 (1H, m, Ar), 8.08 (1H, d, J = 2.1 Hz, Ar), 7.69~7.63 (1H, m, Ar), 7.36 (1H, d, J = 8.1 Hz, Ar), 7.26~7.05 (1H, m, Ar), 6.78 (1H, t, J = 75 Hz, —CHF$_2$), 3.99 (2H, d, J = 6.9 Hz, —OCH$_2$—), 2.75 (3H, s, —CH$_3$), 2.36 (3H, s, —CH$_3$), 1.37~1.25 (1H, m, —CH—), 0.72~0.66 (2H, m, —CH$_2$—), 0.42~0.36 (2H, m, —CH$_2$—). |
| 137 | 5-[7-{3-(Cyclopropylmethoxy)-4-(difloromethoxy)phenyl}-[1,2,4]triazolo[1,5-a]pyrimidine- | $^1$H NMR (300 MHz, CD$_3$OD) δ 9.43 (1H, s, Ar), 8.90 (1H, m, Ar), 8.68 (1H, m, Ar), 8.20 (1H, s, Ar), 8.08 (1H, s, Ar), 7.87 (1H, m, Ar), 7.57 (1H, m, Ar,) 7.40 (1H, m, Ar), 6.98 (1H, t, J = 75.0 Hz, —CHF$_2$), |

TABLE 1-continued

| IUPAC name | | $^1$H NMR |
|---|---|---|
| | 2-yl]pyridine-2-carboxylic acid | 4.06 (2H, d, J = 6.9 Hz, —OCH$_2$—), 1.40~1.32 (1H, m, —CH—), 0.69~0.64 (2H, m, —CH$_2$—), 0.46~0.42 (2H, m, —CH$_2$—). |
| 138 | 5-[7-{3-Cyclopropylmethoxy)-4-(difluoromethoxy)phenyl}-[1,2,4]triazolo[1,5-a]pyrimidine-2-yl]pyridine-2-carboxylic acid methyl ester | $^1$H NMR (300 MHz, CDCl$_3$) δ 9.67 (1H, d, J = 2.1 Hz, Ar), 8.90 (1H, d, J = 4.8 Hz, Ar), 8.77 (1H, m, Ar), 8.29 (1H, d, J = 8.1 Hz, Ar), 8.01 (1H, d, J = 1.8 Hz, Ar), 7.66 (1H, m, Ar) 7.42 (1H, d, J = 8.4 Hz, Ar), 7.28 (1H, d, J = 4.8 Hz, Ar), 6.81 (1H, t, J = 74.7 Hz, —CHF$_2$), 4.06 (3H, s, —COOCH$_3$), 4.02 (2H, d, J = 6.9 Hz, —OCH$_2$—), 1.46~1.33 (1H, m, —CH—), 0.75~0.69 (2H, m, —CH$_2$—), 0.45~0.40 (2H, m, —CH$_2$—). |
| 139 | 5-[7-{3-(cyclopropylmethoxy)-4-(difluoromethoxy)phenyl}-[1,2,4]triazolo[1,5-a]pyrimidine-2-yl]pyridine-2-carboxamide | $^1$H NMR (300 MHz, DMSO-d$_6$) δ 9.41 (1H, d, J = 1.2 Hz, Ar), 9.00 (1H, d, J = 4.8 Hz, Ar), 8.71 (1H, m, Ar), 8.23 (1H, d, J = 8.1 Hz, Ar), 8.06 (1H, d, J = 2.1 Hz, Ar), 7.95 (1H, m, Ar), 7.74 (1H, d, J = 4.5 Hz, Ar), 7.48 (1H, d, J = 8.4 Hz, Ar), 7.32 (1H, t, J = 74.1 Hz, —CHF$_2$), 4.07 (2H, d, J = 6.9 Hz, —OCH$_2$—), 1.44~1.33 (1H, m, —CH—), 0.66~0.60 (2H, m, —CH$_2$—), 0.42~0.37 (2H, m, —CH$_2$—). |
| 140 | 7-[3-(Cyclopropylmethoxy)-4-(difluoromethoxy)phenyl]-2-(4-methylthiophenyl)-[1,2,4]triazolo[1,5-a]pyrimidine | $^1$H NMR (200 MHz, CDCl$_3$) δ 8.80 (1H, d, J = 4.6 Hz, Ar), 8.25 (2H, d, J = 8.4 Hz, Ar), 7.69 (1H, m, Ar), 7.41~7.17 (4H, m, Ar), 6.79 (1H, t, J = 75.0 Hz, —CHF$_2$), 4.03 (2H, d, J = 7.0 Hz, —OCH$_2$—), 2.55 (3H, s, —SCH$_3$), 1.66~1.33 (1H, m, —CH—), 0.76~0.66 (2H, m, —CH$_2$—), 0.46~0.38 (2H, m, —CH$_2$—). |

Analysts of Inhibiting PDE-4 Activity

Experiment of inhibiting PDE-4 activity was carried out by modifying the method of Loughney (Loughney et al., *Journal of Biological Chemistry*, 1996, 271(2), 796-806). Human PDE-4d prepared by means of gene recombination technology was used as PDE-4d The catalytic domain of PDE4d was cloned to pGEX4T3 (APBiotech) as GST fusion expression vector, and then PDE4d gene was transformed to *E. coli* BL21, DE3. The strain was cultured at 37° C. in LB medium, and when OD reached about 0.3~0.5, the temperature was lowered to 18° C. to induce expression of PDE4d by using 0.5 mM IPTG. After 15 hours from induction of the expression, cells with PDE4d expressed were recovered. The cells were suspended in a buffer solution (50 mM Tris, pH 8.0, 0.4M NaCl, 5 mM DTT), and crushed, centrifuged and purified. The columns used for the purification were Q-cephalose (APBiotech), Glutanione-cephalose (APBiotech) and Superdex200 gel permeation chromatography (APBiotech), in this order.

In order to measure the ability of individual compound to inhibit PDE4d activity, PDE4d 1 nM and cAMP (Sigma) 250 nM as substrate were added to the reaction buffer (50 mM Tris-HCl (pH 7.5) and 4 mM MgCl$_2$), and individual compound obtained from Example 1 was added in a concentration from 1 to 50 µM thereto, and the mixture was reacted at 34° C. for 45 minutes. Total reaction solution was 60 µl. As to cAMP, a mixture with the ratio of [$^3$H]cAMP (Amersham, 1 µCi/µl) to cAMP (hot:cold, that is, isotope:non-isotope) being 1:200 was used. Then, the reaction was quenched by heating at 95° C. for 2 minutes. After cooling the mixture for 3 minutes, 1 mg/ml of Snake Venome (Sigma V0376) (30 µl) was added thereto. After reacting at 34° C. for 30 minutes, 30 µl of the reaction mixture was added to 250 µl of DOWEX 1×2-100 ion exchange resin (Aldrich, previously mixed with distilled water in a ratio of 1:1.6) by portions, and the mixture was vigorously stirred for 2 minutes. After settling the resin down, the supernatant (130 µl) was added to 2 ml of scintillation cocktail (Packard), and the mixture was thoroughly mixed, and then measured by using beta-counter. With respect to the enzyme activity of control group (experiment carried out without adding compound of Chemical Formula (1)), the concentration of each test compound to inhibit 50% of enzyme activity was determined as IC$_{50}$. The IC$_{50}$ values of the compounds against PDE-4 enzyme are shown in Table 2.

Table 2

TABLE 2

| Compound No. | IC$_{50}$ (µM) |
|---|---|
| 101 | 0.018 |
| 102 | 0.074 |
| 103 | 0.079 |
| 104 | 0.160 |
| 105 | 0.052 |
| 106 | 0.023 |
| 107 | 0.006 |
| 108 | 0.240 |
| 109 | 0.160 |
| 110 | 0.160 |
| 111 | 0.042 |
| 112 | 0.033 |
| 113 | 0.050 |
| 114 | 0.170 |
| 115 | 0.010 |
| 116 | 0.020 |
| 117 | 0.050 |
| 118 | 0.030 |
| 119 | 0.006 |
| 120 | 0.040 |
| 121 | 0.014 |
| 122 | 0.047 |
| 123 | 0.170 |
| 124 | 0.190 |
| 125 | 0.190 |
| 126 | 0.005 |
| 127 | 0.050 |
| — | — |
| 128 | 0.030 |
| 129 | 0.013 |
| 130 | 0.250 |
| 131 | 0.020 |
| 132 | 0.030 |
| 133 | 0.042 |
| 134 | 0.040 |
| 135 | 0.050 |
| 136 | 0.060 |
| 137 | 0.200 |
| 138 | 0.180 |

TABLE 2-continued

| Compound No. | IC$_{50}$ (μM) |
|---|---|
| 139 | 0.046 |
| 140 | 0.035 |
| — | — |

Test of Therapeutic Activity on Asthma in vivo

For animal test in vivo, 8-9 week old male C57BL/6J mice having body weight of 20-25 g were used as the test animal. For sensitization and challenge of airway and lung by ovalbumin (OVA), OVA mixed with Al(OH)$_3$ was administered intraperitoneally to cause first sensitization, and second sensitization after 10 days from the first sensitization. After 6 days from the second sensitization, the animals were inhaled with 5% OVA via nebulizer for 3 days. Administration of medicine to the sensitized mice was carried out intraorally (po), three times one hour before every inhalation of OVA. To the control group, 0.5% CMC was administered.

In order to observe cell activity and cell constitution in the washing solution of mouse bronchus alveolus, the animal was inhaled with OVA. After 62 hours, the mouse was anesthetized and the cervicothoracic region was open. A tube containing 0.8 ml of PBS was inserted to the bronchus, and PBS was injected. After massaging the chest for about 30 seconds, cell suspension was obtained from the lung. The cells obtained were centrifuged with 400×g. The supernatant was used for measuring eosinophil peroxidase activity (EPO activity), and the pellet was used to examine the cell constituents. For the measurement of EPO activity, the cell suspension (100 ml) was reacted with 0.1 mM OPD, 0.05 M Tris-HCl (pH 8.0), Triton X-100 and 1 mM H2 O$_2$, and then absorbance at 492 nm was measured.

For staining basophil, the cell pellet was resuspended in PBS, and cell-centrifuged at 150×g for 5 minutes in order to get close contact of the cells on the slide. Diff-Quick staining was carried out on the attached cells, and the number of cells was observed under a microscope.

The analysis of airway hyper-responsiveness (AHR) was carried out by using a whole body plethysmographer with a living animal.

After 48 hours from inhalation of OVA, the animal was inhaled with methacholine (Mch) by means of nebulizer. Responsiveness of airway due to Mch was evaluated by enhanced pause (Penh) value on capability of respiration through airway by means of whole body plethysmography, and compared with control medicine.

Procedure for Testing Side-effect Related to Emesis

Male ferrets having the body weight of about 1.5~2 kg, purchased from Marshal, were classified into the groups: control, yohimbine, #102-500 mg/kg and #102-1000 mg/kg treated groups. For three animals in each group, the medicine dissolved in 0.5% CMC at a concentration of 500 and 1000 mg/kg was orally administered. During 3 hours after then, the number of vomiting for each animal, and the number of animals showing salivation and diarrhea were measured by visual observation.

IC$_{50}$ value of the compounds according to the present invention against PDE-4 enzyme was mostly at the level from 0.001 to 0.200 μM. Particularly, Compound (107) exhibited IC$_{50}$ value of 0.006 μM, and Compound (126), 0.005 μM.

The result of test for inhibiting PDE-4 activity showed, as can be seen from Table 2, that the activity of 3',4'-dialkoxyphenyl substituted triazolopyrimidine compounds of Chemical Formula (1) according to the present invention significantly depends on R$_1$ and R$_2$. The compounds of Chemical Formula (1) wherein R$_1$ is substituted by difluoromethyl, and R$_2$ is substituted by cyclopropylmethyl generally showed superior activity on inhibiting PDE-4 to the compounds wherein both R$_1$ and R$_2$ are substituted by difluoromethyl (Compounds 114, 122, 130) (for example, Compound 101 vs. Compound 114 Compound 102 vs. Compound 130 Compound 115 vs. Compound 122). Further, The compounds wherein R$_1$ is substituted by difluoromethyl, and R$_2$ is substituted by cyclopropylmethyl showed superior activity on inhibiting PDE-4 to the compounds wherein R$_1$ is substituted by methyl and R$_2$ are substituted by cyclopentyl (for example, Compound 115 vs. Compound 129 Compound 101 vs. Compound 135).

The compounds of Chemical Formula (1) wherein R$_3$ is phenyl or a pyridine derivative generally showed excellent activity on inhibiting PDE-4, and meta-substituents likely show superior activity to para-substituents (Compound 115 vs. Compound 117 Compound 126 vs. Compound 127 Compound 125 vs. Compound 128). When R$_3$ is pyridine, meta-pyridine and pyridinoxide showed superior inhibiting activity to para-pyridine and pyridinoxide (Compound 101 vs. Compound 103 Compound 102 vs. Compound 110).

The compounds of Chemical Formula (1) wherein R$_3$ is phenyl substituted with X (wherein X is methoxy, cyano, bromo, amino or a carboxylic acid derivative) (Compound 107, 115, 121, 119, 131) showed excellent activity on inhibiting PDE-4, in particular, the compound with iodine substituent (Compound 126) showed most excellent activity.

By using OVA-sensitized C57BL/6J mice, the degree of airway contraction by the compounds of the present invention was evaluated by means of enhanced pause (Penh) value, and compared to that of control medicine. As the result, when orally administered at a dose of 100 mg/kg, the compounds according to the present invention showed superior effect of treating asthma to the control compound, Roflumilast (100 mg/kg, oral administration), as well as excellent effect from the measurement of eosinophil peroxidase activity (EPO activity).

The results obtained from representative compounds via above-described investigations by using OVA-sensitized C57BL/6J mice, as comparing the degree of airway contraction evaluated by means of enhanced pause (Penh) value to that of control medicine, were shown in FIG. 1 (Compound 102). As the result, the compounds according to the present invention showed superior effect of treating asthma at a dose not less than 25 mg/kg. In particular, when orally administered at a dose of 100 mg/kg, Compound (102) showed far superior effect of treating asthma to the control compound, Roflumilast (100 mg/kg, oral administration).

Moreover, as shown from FIG. 2, the result of eosinophil peroxidase activity (EPO activity) showed excellent effect when Compound (102) was orally administered at a dose of 5, 50, 100 and 300 mg/kg, respectively.

As the result of the test of side-effect related to emesis, the compounds according to the present invention did not show any disorder upon oral administration both at 500 mg/kg and 1,000 mg/kg dose. On the other hand, in the yohimbine treated group (7 mg/kg of dose), vomiting symptoms (average twice) were observed in all ferrets used, with 66% of the animals showing salivation and diarrhea.

Industrial Applicability

The compounds, 7-(3',4'-dialkoxyphenyl)-[1,2,4]triazolo[1,5-a]pyrimidine, according to the present invention are novel compounds having novel chemical structure, and exhibit excellent activity on PDE-4 enzyme and high specificity against other PDE enzymes. Further, as the animal test of asthma model by using the compounds showed, the compounds exhibited excellent effect on treating asthma, so that they are usable as a therapeutic agent for inflammatory diseases including asthma and chronic obstructive pulmonary disease. Moreover, since the most troublesome issue of PDE-4 inhibitors, that is of side effects related to vomiting, was greatly overcome according to the present invention, the compounds can be used for treating or preventing inflammatory diseases including asthma and chronic obstructive pulmonary disease, as well as arthritis, atopic dermatitis, cancers including leukemia, and degenerative brain diseases including Alzheimer's disease, depression and memory impairment, on the basis of PDE-4 inhibition.

The invention claimed is:

1. A compound represented by Chemical Formula 1, or pharmaceutically acceptable salts thereof:

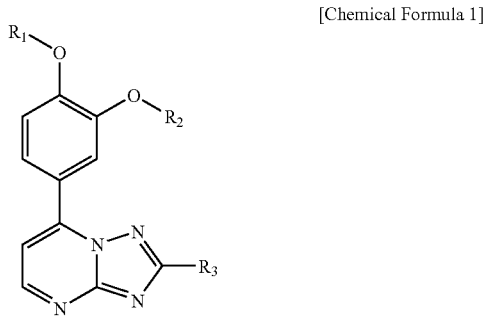

[Chemical Formula 1]

wherein in Chemical Formula (1),
$R_1$ and $R_2$, being same or different, independently represent hydrogen atom, a linear or branched, saturated or unsaturated $(C_1-C_7)$alkyl, a linear or branched, saturated or unsaturated $(C_1-C_7)$alkyl containing halogen atom(s), $(C_3-C_7)$cycloalkyl, or $(C_3-C_7)$cycloalkyl$(C_1-C_7)$alkyl, $R_3$ represents an aryl group represented by one of the following Chemical Formulas:

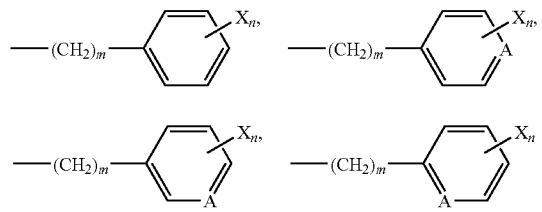

wherein A is N or NO;
m and n independently represent an integer from 0 to 4;
X, being same or different, independently represents a linear or branched, saturated or unsaturated $(C_1-C_7)$ alkyl, $(C_1-C_7)$alkoxy, $(C_1-C_7)$alkylthio, $(C_1-C_7)$alkoxy $(C_1-C_7)$alkyl, $(C_1-C_7)$alkoxycarbonyl, $(C_1C_1-C_7)$ alkoxycarbonyl$(C_1-C_7)$alkoxy, $(C_{1-}C_7)$alkoxycarbonyl $(C_1-C_7)$alkylamino, $(C_1-C_7)$alkoxycarbonyl$(C_1-C_7)$ alkylaminocarbonyl, $(C_1-C_7)$alkylcarbonyloxy$(C_1-C_7)$ alkoxycarbonyl, hydroxy, halogen, cyano, nitro, amino, mono or di$(C_1-C_7)$alkylamino, mono or di$(C_1-C_7)$alkylaminocarbonyl, $(C_3-C_7)$cycloalkylamino, $(C_1-C_7)$alkylcarbonylamino, aminocarbonyl, morpholine, morpholine oxide, piperazine, piperazine oxide, guanidine, urea, $(C_1-C_7)$alkylguanidine, $(C_1-C_7)$alkylurea, phenyl, phenoxy, benzyl, benzyloxy, thiobenzyl, carboxylic acid, carboxyl$(C_1-C_7)$alkylamino, $(C_1-C_7)$alkylcarbonyl, or benzoyl;

provided that $(C_1-C_7)$alkyl, $(C_3-C_7)$cycloalkyl, $(C_3-C_7)$cycloalkyl$(C_1-C_7)$alkyl, phenyl or benzyl in $R_1$, $R_2$, $R_3$ and X may be substituted with $(C_1-C_7)$alkoxy, halogen, nitro, cyano, hydroxy, amino, or carboxylic acid.

2. The compound or pharmaceutically acceptable salts thereof according to claim 1, wherein $R_1$ is a linear or branched, unsaturated $(C_1-C_7)$alkyl containing halogen atom(s); $R_2$ is linear or branched, saturated or unsaturated $(C_1-C_7)$alkyl, cyclopropyl, cyclopentyl or cyclopropylmethyl; X is a linear or branched, saturated or unsaturated $(C_1-C_7)$alkyl, linear or branched, unsaturated $(C_1-C_7)$alkyl containing halogen atom(s), $(C_1-C_7)$alkoxy, $(C_1-C_7)$alkylthio, $(C_1-C_7)$alkoxycarbonyl, hydroxy, halogen, cyano, nitro, amino, mono or di$(C_1-C_7)$alkylamino, mono or di$(C_1-C_7)$alkylaminocarbonyl, $(C_1-C_7)$alkylcarbonylamino, aminocarbonyl, phenyl, phenoxy, benzyl, benzyloxy, thiobenzyl or carboxylic acid and n is an integer from 0 to 3.

3. A compound represented by Chemical Formula 2 or pharmaceutically acceptable salts thereof:

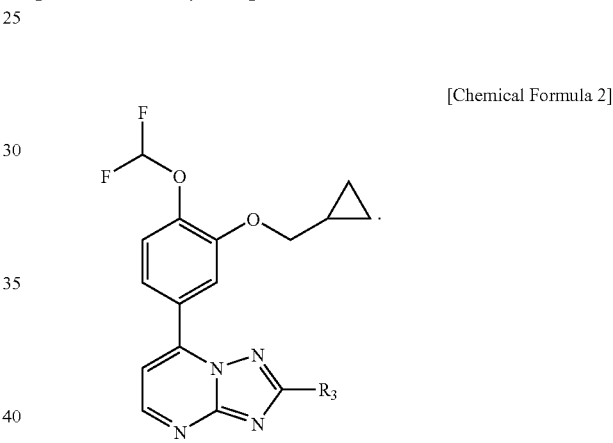

[Chemical Formula 2]

wherein $R_3$ is an aryl group represented by one of the following Chemical Formulas;

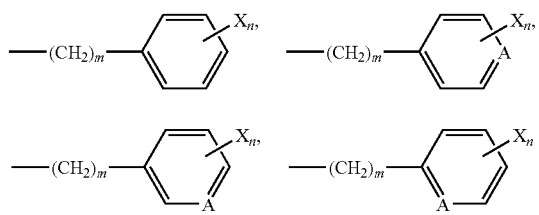

wherein, A is N or NO;
m and n independently represent an integer from 0 to 3; and
X, being same or different, independently represents a linear or branched, saturated or unsaturated $(C_1-C_7)$ alkyl, a linear or branched, unsaturated $(C_1-C_7)$alkyl containing halogen atom(s), $(C_1-C_7)$alkoxy, $(C_1-C_7)$ alkylthio, $(C_1-C_7)$alkoxycarbonyl, halogen, cyano, nitro, amino, aminocarbonyl or carboxylic acid.

4. A compound represented by Chemical Formula 3 or pharmaceutically acceptable salts thereof:

[Chemical Formula 3]

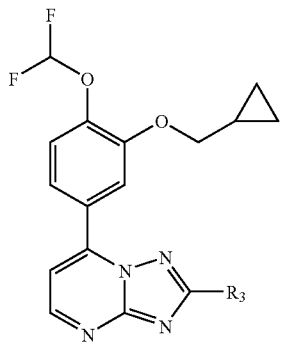

wherein R₃ is an aryl group selected from following Chemical Formulas:

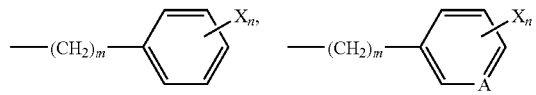

wherein, A is N or NO;
m and n independently represent an integer of 0 or 1; and
X, being same or different, independently represents ($C_1$-$C_7$)alkoxy, halogen, cyano, nitro, amino or carboxylic acid.

5. The compound or pharmaceutically acceptable salts thereof according to claim 4, which is selected from following compounds:

7-[3-(cyclopropylmethoxy)-4-(difluoromethoxy)phenyl]-2-(pyridin-3-yl)-[1,2,4]triazolo[1,5-a]pyrimidine
3-[7-{3-(cyclopropylmethoxy)-4-(difluoromethoxy)phenyl}-[1,2,4]triazolo[1,5-a]pyrimidin-2-yl]-pyridinium chloride
7-[3-(cyclopropylmethoxy)-4-(difluoromethoxy)phenyl]-2-(3-methoxyphenyl)-[1,2,4]triazolo[1,5-a]pyrimidine
3-[7-{3-(cyclopropylmethoxy)-4-(difluoromethoxy)phenyl}-[1,2,4]triazolo[1,5-a]pyrimidine-2-yl]-pyridine-N-oxide
7-[3-(cyclopropylmethoxy)-4-(difluoromethoxy)phenyl]-2-(3-iodophenyl)-[1,2,4]triazolo[1,5-a]pyrimidine
2-(3-cyanophenyl)-7-[3-(cyclopropylmethoxy)-4-(difluoromethoxy)phenyl]-[1,2,4]triazolo[1,5-a]pyrimidine
3-[7-{3-(cyclopropylmethoxy)-4-(difluoromethoxy)phenyl}-[1,2,4]triazolo[1,5-a]pyrimidin-2-yl]benzoic acid
2-(3-aminophenyl)-7-]3-(cyclopropylmethoxy)-4-(difluoromethoxy)phenyl]-[1,2,4]triazolo[1,5-a]pyrimidine.

6. A process for preparing 7-(3',4'-dialkoxyphenyl)-[1,2,4]triazolo[1,5-a]pyrimidine, wherein 3-amino-triazole compound (4) is reacted with 3-(dimethylamino)-1-(3,4-dialkoxyphenyl)propenone compound (5) or 3-(3,4-dialkoxyphenyl)-3-oxopropionaldehyde compound (6) in the presence of acetic acid to obtain the compound of Chemical Formula (1) according to claim 1,

[Reaction Scheme 1]

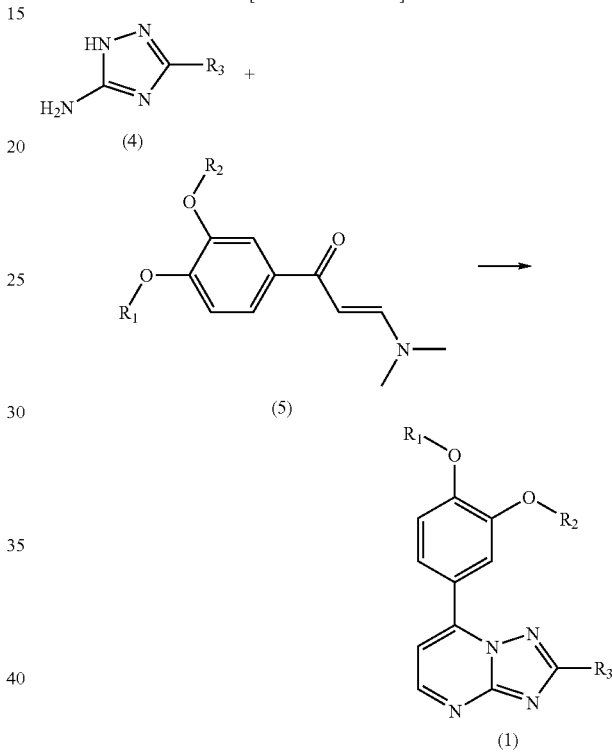

wherein, R₁, R₂ and R₃ are defined as in claim 1.

7. A pharmaceutical composition which comprises a compound of Chemical Formula (1) or pharmaceutically acceptable salts thereof according to claim 1, as an active ingredient in a pharmaceutically acceptable carrier.

* * * * *

UNITED STATES PATENT AND TRADEMARK OFFICE
CERTIFICATE OF CORRECTION

| | |
|---|---|
| PATENT NO. | : 8,143,262 B2 |
| APPLICATION NO. | : 12/531818 |
| DATED | : March 27, 2012 |
| INVENTOR(S) | : Dong Ju Jeon et al. |

Page 1 of 1

It is certified that error appears in the above-identified patent and that said Letters Patent is hereby corrected as shown below:

On the Title Page:

Column 1, Item (54), Lines 1-2, ")[1,2,4]" should read -- )-[1,2,4] --

Column 2, OTHER PUBLICATIONS, insert -- Dorwald F. A. Side Reactions in Organic Synthesis, 2005, Wiley: VCH, Weinheim pg. IX of Preface. --

Column 2, OTHER PUBLICATIONS, delete "Petrich, et al., The Application of Unsymmetrical Vinylogous Iminium Salts and Related Synthons to the Preparation of Monosubstituted Triasolo [1,5-a] pyrimidines, Tetrahedron, Elsevier Science Publishers, (Jan. 1, 1994), vol. 50, No. 42, pp. 12113-12124."

In the Specifications:

Column 1, Line 1, ")[1,2,4]" should read -- )-[1,2,4] --

In the Claims:

Column 29, Line 58, Claim 1, delete "($C_1C_1$-$C_7$)alkoxycarbonyl($C_1$-$C_7$)alkoxy" and insert -- ($C_1$-$C_7$)alkoxycarbonyl($C_1$-$C_7$)alkoxy --

Column 29, Line 59, Claim 1, delete "($C_1$-$C_7$)alkoxycarbonyl($C_1$-$C_7$)alkylamino" and insert -- ($C_1$-$C_7$)alkoxycarbonyl($C_1$-$C_7$)alkylamino --

Signed and Sealed this
Third Day of July, 2012

David J. Kappos
*Director of the United States Patent and Trademark Office*